(12) United States Patent
Pelletier

(10) Patent No.: US 7,538,113 B2
(45) Date of Patent: *May 26, 2009

(54) 4-SUBSTITUTED IMIDAZO[4,5-C]PYRIDINE ANTAGONISTS OF GONADOTROPIN RELEASING HORMONE RECEPTOR

(75) Inventor: Jeffrey C. Pelletier, Lafayette Hill, PA (US)

(73) Assignee: Wyeth, Madison, NJ (US)

( * ) Notice: Subject to any disclaimer, the term of this patent is extended or adjusted under 35 U.S.C. 154(b) by 341 days.

This patent is subject to a terminal disclaimer.

(21) Appl. No.: 11/354,621

(22) Filed: Feb. 15, 2006

(65) Prior Publication Data

US 2006/0189618 A1    Aug. 24, 2006

Related U.S. Application Data

(60) Provisional application No. 60/654,560, filed on Feb. 18, 2005.

(51) Int. Cl.
*A61K 31/497* (2006.01)
*C07D 401/00* (2006.01)

(52) U.S. Cl. .......................... 514/252.14; 514/253.04; 544/362

(58) Field of Classification Search ............ 514/252.14, 514/253.04; 544/362
See application file for complete search history.

(56) References Cited

U.S. PATENT DOCUMENTS

| | | | |
|---|---|---|---|
| 3,325,506 A | 6/1967 | Jones et al. |
| 3,996,233 A | 12/1976 | Denzel et al. |
| 4,459,296 A | 7/1984 | Ancher et al. |
| 4,833,142 A | 5/1989 | Hartog et al. |
| 5,057,517 A | 10/1991 | Johnston et al. |
| 5,338,740 A | 8/1994 | Carpino et al. |
| 5,424,313 A | 6/1995 | Hartog et al. |
| 5,502,187 A | 3/1996 | Ayer et al. |
| 5,576,460 A | 11/1996 | Buchwald et al. |
| 5,643,944 A | 7/1997 | Garfield et al. |
| 5,716,964 A | 2/1998 | Hansen, Jr. et al. |
| 6,277,989 B1 | 8/2001 | Chakravarty et al. |
| 6,306,859 B1 | 10/2001 | Childers et al. |
| 6,307,087 B1 | 10/2001 | Buchwald et al. |
| 6,310,066 B1 | 10/2001 | Kelly et al. |
| 6,313,126 B1 | 11/2001 | Mewshaw et al. |
| 6,376,141 B1 | 4/2002 | Mishra et al. |
| 6,399,629 B1 | 6/2002 | Chamberland et al. |
| 6,476,031 B1 | 11/2002 | Chakravarty et al. |
| 6,492,517 B1 | 12/2002 | Burdeniuc |
| 6,548,505 B1 | 4/2003 | Martin et al. |
| 6,559,167 B1 | 5/2003 | Garst et al. |
| 6,620,529 B1 | 9/2003 | Ise et al. |
| 6,696,469 B2 | 2/2004 | Peglion et al. |
| 6,723,724 B2 | 4/2004 | Koh et al. |
| 6,821,967 B2 | 11/2004 | Lehmann-Lintz et al. |
| 6,841,549 B1 | 1/2005 | Asano et al. |
| 2001/0020030 A1 | 9/2001 | Stewart et al. |
| 2002/0013324 A1 | 1/2002 | Childers et al. |
| 2002/0055133 A1 | 5/2002 | Hahn et al. |
| 2002/0072053 A1 | 6/2002 | McNally et al. |
| 2002/0147197 A1 | 10/2002 | Newman et al. |
| 2002/0161010 A1 | 10/2002 | Chakravarty et al. |
| 2002/0168630 A1 | 11/2002 | Fleming et al. |
| 2002/0182623 A1 | 12/2002 | Lefevre et al. |
| 2003/0021851 A1 | 1/2003 | Goswami et al. |
| 2003/0028018 A1 | 2/2003 | Renhowe et al. |
| 2003/0051260 A1 | 3/2003 | Chada et al. |
| 2003/0055057 A1 | 3/2003 | Blume et al. |
| 2003/0069248 A1 | 4/2003 | Chakravarty et al. |
| 2003/0165920 A1 | 9/2003 | Chou et al. |
| 2003/0220365 A1 | 11/2003 | Stewart et al. |
| 2004/0018240 A1 | 1/2004 | Ohmachi et al. |
| 2004/0036868 A1 | 2/2004 | Jones et al. |
| 2004/0082635 A1 | 4/2004 | Hashimoto et al. |
| 2004/0082798 A1 | 4/2004 | Alonso-Alija et al. |
| 2004/0102502 A1 | 5/2004 | Watanabe et al. |
| 2004/0121008 A1 | 6/2004 | Shiraishi et al. |
| 2004/0122001 A1 | 6/2004 | Agejas-Chicharro et al. |
| 2004/0219208 A1 | 11/2004 | Kawamura et al. |
| 2005/0009894 A1 | 1/2005 | Babin et al. |
| 2005/0065196 A1 | 3/2005 | Inaba et al. |
| 2005/0101647 A1 | 5/2005 | Oda et al. |
| 2005/0282820 A1 | 12/2005 | Gontcharov et al. |
| 2006/0019965 A1 | 1/2006 | Garrick et al. |
| 2006/0111355 A1 | 5/2006 | Garrick et al. |
| 2006/0189616 A1 * | 8/2006 | Pelletier et al. ............ 514/248 |
| 2006/0189617 A1 * | 8/2006 | Pelletier et al. ............ 514/248 |
| 2006/0189618 A1 | 8/2006 | Pelletier |
| 2006/0189619 A1 | 8/2006 | Tadayon et al. |
| 2006/0264631 A1 | 11/2006 | Green et al. |
| 2006/0270848 A1 | 11/2006 | Lundquist et al. |

FOREIGN PATENT DOCUMENTS

| | | |
|---|---|---|
| DE | 39 26 770 A1 | 2/1991 |
| DE | 10030376 | 1/2002 |
| DE | 10110750 | 9/2002 |
| DE | 20217340 | 2/2003 |
| EP | 0138280 | 4/1985 |

(Continued)

OTHER PUBLICATIONS

U.S. Appl. No. 11/355,298, filed Feb. 15, 2006, Pelletier et al.
U.S. Appl. No. 11/354,793, filed Feb. 15, 2006, Pelletier et al.
Barraclough et al. "Inotropic 'A' Ring Substituted Sulmazole and Isomazole Analogues," J. Med. Chem., 1999, 33, 2231-2239.

(Continued)

*Primary Examiner*—James O Wilson
*Assistant Examiner*—Erich A Leeser
(74) *Attorney, Agent, or Firm*—Wilmer Cutler Pckering Hale and Dorr LLP

(57) ABSTRACT

The present invention relates to Gonadotropin Releasing Hormone (GnRH, also known as Luteinizing Hormone Releasing Hormone) receptor antagonists.

17 Claims, No Drawings

FOREIGN PATENT DOCUMENTS

| | | |
|---|---|---|
| EP | 0 300 726 B1 * | 7/1988 |
| EP | 0 300 726 | 1/1989 |
| EP | 0 400 974 | 12/1990 |
| EP | 0 434 038 | 6/1991 |
| EP | 0 471 236 B1 | 2/1992 |
| EP | 1136483 | 9/2001 |
| EP | 1197485 | 4/2002 |
| EP | 1239283 | 9/2002 |
| GB | 1009807 | 11/1965 |
| GB | 1049330 | 11/1966 |
| GB | 2097790 | 11/1983 |
| GB | 2369616 | 6/2002 |
| GB | 2370270 | 6/2002 |
| IT | 01298727 | 2/2000 |
| JP | 2002161084 | 6/2002 |
| JP | 2002193946 | 7/2002 |
| JP | 2002212101 | 7/2002 |
| JP | 2003040890 | 2/2003 |
| JP | 2003083968 | 3/2003 |
| JP | 2003231687 | 8/2003 |
| NL | 6409237 | 4/1965 |
| NL | 6413475 | 5/1965 |
| RU | 2182708 | 5/2002 |
| WO | WO 93/20078 | 10/1993 |
| WO | WO 99/07703 | 2/1999 |
| WO | WO 99/16755 | 4/1999 |
| WO | WO-9955672 | 11/1999 |
| WO | WO 99/62908 | 12/1999 |
| WO | WO-0002887 | 1/2000 |
| WO | WO 00/12089 | 3/2000 |
| WO | WO-0040554 | 7/2000 |
| WO | WO-0102369 | 1/2001 |
| WO | WO 01/49688 | 7/2001 |
| WO | WO-0147898 | 7/2001 |
| WO | WO-0157038 | 8/2001 |
| WO | WO 01/70743 | 9/2001 |
| WO | WO-0170728 | 9/2001 |
| WO | WO 01/74786 | 10/2001 |
| WO | WO-0208221 | 1/2002 |
| WO | WO-0208245 | 1/2002 |
| WO | WO-0214859 | 2/2002 |
| WO | WO-0218383 | 3/2002 |
| WO | WO-0221135 | 3/2002 |
| WO | WO-0222598 | 3/2002 |
| WO | WO-0222600 | 3/2002 |
| WO | WO 02/32422 | 4/2002 |
| WO | WO-0228839 | 4/2002 |
| WO | WO-0230935 | 4/2002 |
| WO | WO-0234263 | 5/2002 |
| WO | WO-0235474 | 5/2002 |
| WO | WO-0236562 | 5/2002 |
| WO | WO-0240019 A1 | 5/2002 |
| WO | WO-0240653 | 5/2002 |
| WO | WO-0241906 | 5/2002 |
| WO | WO-0242292 | 5/2002 |
| WO | WO-0243709 | 6/2002 |
| WO | WO-0244168 | 6/2002 |
| WO | WO-0244170 | 6/2002 |
| WO | WO-0245707 | 6/2002 |
| WO | WO-0248152 | 6/2002 |
| WO | WO-0250062 | 6/2002 |
| WO | WO 02/051409 | 7/2002 |
| WO | WO-02055012 | 7/2002 |
| WO | WO-02055013 | 7/2002 |
| WO | WO-02059088 | 7/2002 |
| WO | WO-02062949 | 7/2002 |
| WO | WO-02064590 | 8/2002 |
| WO | WO 02/072549 | 9/2002 |
| WO | WO-02068399 | 9/2002 |
| WO | WO-02069901 | 9/2002 |
| WO | WO-02071073 | 9/2002 |
| WO | WO-02074340 | 9/2002 |
| WO | WO-02083952 | 9/2002 |
| WO | WO 02/081463 | 10/2002 |
| WO | WO-02076439 | 10/2002 |
| WO | WO-02076926 | 10/2002 |
| WO | WO-02076947 | 10/2002 |
| WO | WO-02076960 | 10/2002 |
| WO | WO-02076976 | 10/2002 |
| WO | WO-02079192 | 10/2002 |
| WO | WO-02079690 | 10/2002 |
| WO | WO-02083143 | 10/2002 |
| WO | WO-02083608 | 10/2002 |
| WO | WO-02089738 | 11/2002 |
| WO | WO-02101087 | 11/2002 |
| WO | WO-02102774 | 12/2002 |
| WO | WO-02102978 | 12/2002 |
| WO | WO 03/007945 | 1/2003 |
| WO | WO-03004023 | 1/2003 |
| WO | WO-03004488 | 1/2003 |
| WO | WO-03013488 | 2/2003 |
| WO | WO-03013609 | 2/2003 |
| WO | WO 03/022214 | 3/2003 |
| WO | WO-03018835 | 3/2003 |
| WO | WO-03021851 | 3/2003 |
| WO | WO-03024401 | 3/2003 |
| WO | WO-03025563 | 3/2003 |
| WO | WO-03026664 | 4/2003 |
| WO | WO-03026665 | 4/2003 |
| WO | WO-03026666 | 4/2003 |
| WO | WO-03027223 | 4/2003 |
| WO | WO-03031436 | 4/2003 |
| WO | WO-03032984 | 4/2003 |
| WO | WO 03/035065 | 5/2003 |
| WO | WO-03035644 | 5/2003 |
| WO | WO-03037871 | 5/2003 |
| WO | WO-03037872 | 5/2003 |
| WO | WO-03038401 | 5/2003 |
| WO | WO-03048140 | 6/2003 |
| WO | WO-03053939 A1 | 7/2003 |
| WO | WO-03053948 | 7/2003 |
| WO | WO-03068754 | 8/2003 |
| WO | WO-03070943 | 8/2003 |
| WO | WO-03082272 | 10/2003 |
| WO | WO-03091408 | 11/2003 |
| WO | WO-03095432 | 11/2003 |
| WO | WO-03095995 | 11/2003 |
| WO | WO 2004/016611 | 2/2004 |
| WO | WO-04035549 | 4/2004 |

OTHER PUBLICATIONS

Armer and Smelt, "Non_peptidic GnRh Receptor Antagonists," Current Medicinal Chemistry, vol. 11, pp. 3017-3028 (2004).

Artamonova, et al., "Preparation of 1,5-Disubstituted Tetrazoles Under Phase-Transfer Conditions", Synthesis (1996) 12, 1428-30.

Buchwald, et al., "Long-term, Continuous Intravenous Heparin Administration by an Implantable Infusion Pump in Ambulatory Patients with Recurrent Venous Thrombosis", Surgery, 88(4):507-516 (1980).

Bundgaard, "Design and Application of Prodrugs", in *Textbook of Drug Design and Development*, Kgrogsgaard-Larsen, et al., eds., Harwood Academic Publishers, Chapter 5, pp. 113-191 (1991).

Chengalvala, M.V. et al., "GnRH Agonists and Antagonists in Cancer Therapy," Curr. Med. Chem.—Anti-Cancer Agents, 2003, 3, 399-410.

Clayton, et al., "Receptor-binding Affinity of Gonadotropin-releasing Hormone Analogs: Analysis by Radioligand-receptor Assay", Endocrinology, 106(4):1154-1159 (1980).

Controlled Drug Bioavailability, Drug Product Design and Performance, Smolen, et al., eds., John Wiley & Sons (1984).

Dandegaonker, et al., "Brom-hydroxychalkone", Monatshefte fuer Chemie 96(2), (1965) 450-60.

Decroix, et al., "Synthese de Composes Polyazotes a Partir de Nitrile ou D'iminoether Furannique, Thiophenique et Selenophenique", Bulletin de la Societe Chimique de France (1976) (3-4, Pt. 2) 621-7.
*Design of Prodrugs*, Bundgaard, ed., Elsevier (1985).
Dorwald F.A., *Side Reactions in Organic Synthesis*, Wiley: VCH Weinheim, p. IX of Preface (2005).
Dox, A.W. "Acetamidine Hydrochloride," Organic Syntheses, 1932, pp. 5-7.
During, et al., "Controlled Release of Dopamine from a Polymeric Brain Implant: In Vivo Characterization", Ann. Neural., 25(4):351-356 (1989).
Edlin, et al., "Selective Solvent Extraction of Tetrahedrally-Coordinating Transition Metal Ions From Acidic Aqueous Media Using Benzimidazole-Phosphinate Ligands: Specificity for Zinc(II) Over Copper(II)", New Journal of Chemistry 23(8) (1999) 819-26.
Enuguehard, et al., Ipso- or Cine-Substitutions of 6-Haloimidazo [1,2-a]pyridine Derivatives with Different Azoles Depending on the Reaction Conditions, J. Org. Chem, 68:5614-5617 (2003).
Finkelstein, "Regioselective Lithiation and Reaction of [1,2,4]Triazolo[1,5-a]pyridine and Pyrazolo[1,5-a]pyridine", J. Org. Chem., 57:5538-5540 (1992).
Gilchrist, et al., "Cyclisations of Ortho-Substituted N-Arylbenzimidoyl Nitrenes. Part 1. Cyclisations With Ortho-Alkyl Substituents: Skeletal Rearrangements and [1,9]Alkyl Migrations", J. Chem. Soc. Perkin Trans. I (1979) 1871-73.
Goodson, "Dental Applications", *Medical Applications of Controlled Release*, vol. 2, Langer, et al,. eds., CRC Press, Boca Raton, FL, pp. 115-138 (1984).
Grenda, et al., "Novel Preparation of Benzimidazoles From N-Arylamidines. New Synthesis of Thiabendazole", J. Org. Chem. (1965) 30(1) 259-61.
Grundker, C. et al., "Gonadotropin-releasing hormone receptor-targeted gene therapy of gynecologic cancers," Molecular Cancer Therapeutics 2005; 4(2). Feb. 2005, 225-231.
Gudmundsson, et al., "Synthesis of Novel Imidazo[1,2-a]pyridines with Potent Activity Against Herpesviruses", Org. Lett, 5(8):1369-1372 (2003).
Harris, et al., "Improved Functional Group Compatibility in the Palladium-Catalyzed Synthesis of Aryl Amines", Org. Lett. (2002) 4, 2885-8.
Haruki et al., "The Preparation of 2-Substituted Benzimidazoles and 2-Phenylnaphtho-[1,2-d]imidazole From N-Arylamidines", Bull. Chem. Soc. Japan (1965) 38(10), 1805.
Haruki, et al., "Some Reactions of N-Haloamidines", Bull. Chem. Soc. Japan (1968) 41, 1361-67.
Hirsch, L. et al., "Birth Control: Birth Control Pill," TeensHealth, Nemours Foundation, http://kidshealth.org/teen/sexual_health/contraception/contraception_birth.html, Jul. 2, 2008.
Hisano, et al., "Synthesis of Benzoxazoles, Benzothiazoles and Benzimidazoles and Evaluation of Their Antifungal, Insecticidal and Herbicidal Activities", Chem. Pharm. Bull. (1982) 30(8), 2996-3004.
Howard III, et al., "Intracerebral Drug Delivery in Rats with Lesion-Induced Memory Deficits", J. Neurosurg., 71:105-112 (1989).
Ichikawa, et al., "Acidic Properties of Benzimidazoles and Substituent Effects. III: The Substituent Effect on the Imidazole Cyclization From N-(m-Substituted-Phenyl) Picolylamidines", Organic Preparations and Procedures International (1979) 10(5), 205-9.
Ichikawa, et al., "Acidic Properties of Benzimidazoles and Substituent Effects. IV. Relationship Between the Acidities of N'-(Substituted Phenyl) Arylamidines and Ring Closures to Imidazole", Chem. Pharm. Bull. (1979) 27(5), 1255-64.
Katritzky, et al., "Pyrazolo(1,5-c)Pyrimidines From Pyrylium Salts And Amidrazones And Pyridine Imidoyl-N-Imides From Imidoyl Chlorides", Heterocycles (1982) 18, 21-28.
Langer, "New Methods of Drug Delivery", Science, 249:1527-1533 (1990).
Langer, et al., "Chemical and Physical Structure of Polymers as Carriers for Controlled Release of Bioactive Agents: A Review", J. Macromol. Sci. Rev. Macromol. Chem., C23(1):61-126 (1983).

Levy, et al., "Inhibition of Calcification of Bioprosthetic Heart Valves by Local Controlled-Release Diphosphonate", Science, 228:190-192 (1985).
Liu, et al., "A Particularly Convenient Preparation of Benzohydroximinoyl Chlorides (Nitrile Oxide Precursors)", J. Org. Chem. (1980) 45, 3916-18.
Lopez-Berestein, "Treatment of Systemic Fungal Infections with Liposomal-Amphotericin B", *Liposomes in the Therapy of Infectious Diseases and Cancer*, Lopez-Berstein, et al., eds., Alan R. Liss, Inc., New York, pp. 317-327 (1989).
López-Rodriguez, et al., "Design and Synthesis of New Benzimidazole-Arylpiperazine Derivatives Acting as Mixed 5-HT$_{1A}$/5-HT$_3$ Ligands", Bioorg. & Med. Chem. Letters (2003) vol. 13, 3177-80.
López-Rodriguez, et al., "Design and Synthesis of S-(-)-2-[[4-(napht-1-yl)piperazin-1-yl]-methyl]-1,4-dioxoperhydropyrrolo[1,2-a]pyrazine (CSP-2503) Using Computational Simulation. A 5-HT$_{1A}$ Receptor Agonist", Bioorg. & Med. Chem. Letters (2003) vol. 13, 1429-32.
López-Rodriguez, et al., "Pd(0) Amination of Benzimidazoles as an Efficient Method towards New (Benzimidazolyl) piperazines with High Affinity for the 5-HT$_{1A}$ Receptor", Tetrahedron 56 (2000) 3245-53.
López-Rodriguez, et al., "Synthesis of New (Benzimidazolyl) Piperazines with Affinity for the 5-HT$_{1A}$ Receptor Via Pd(0) Amination of Bromobenzimidazoles", Bioorg. & Med. Chem. Letters (1999) vol. 9, 2339-42.
March, Advanced Organic Chemistry: Reactions, Mechanisms and Structures, Fourth Edition, John Wiley & Sons, pp. 69-74 (1992).
*Medical Applications of Controlled Release*, vol. I and II, Langer and Wise, eds., CRC Press, Inc., Boca Raton, FL (1984).
*Methods in Enzymology*, vol. 112, Widder, et al., eds., Academic Press (1985).
Mewshaw, et al., "New Generation Dopaminergic Agents. 5. Heterocyclic Bioisosteres That Exploit The 3-OH-N$^1$-Phenylpiperazine Dopaminergic Template", *Bioorg. & Med. Chem. Letters* (1998) vol. 8, 2675-80.
Nielsen, et al., "Glycolamide Esters as Biolabile Prodrugs of Carboxylic Acid Agents: Synthesis, Stability, Bioconversion, and Physiochemical Properties", Journal of Pharmaceutical Sciences, 77(4):285-298 (1988).
Partridge, et al., "Cyclic Amidines. Part VII. Preparation of Benziminazoles From N'-Aryl-N-Hydroxyamidines", J. Chem. Soc. (1958) 2086-92.
*Prodrugs as Novel Drug Delivery Systems*, Higuchi, et al., eds., American Chemical Society, Washington, DC (1975).
Radebaugh, et al., "Preformulation", *Remington: The Science and Practice of Pharmacy*, 19th Edition, Gennaro, Ed., pp. 1447-1462 (1995).
Ramsden, et al., "Rearrangement and Cyclo-☐-Elimination of N-Substituted Amidines Using (Diacetoxyiodo) Benzene", J. Chem. Soc. Perkin Trans. I (1995) 615-17.
Saudek, et al., "A Prelminiary Trial of the Programmable Implantable Medication System for Insulin Delivery", New England Journal of Med., 321(9):574-579 (1989).
Sefton, "Implantable Pumps", CRC Crit. Ref. Biomed. Eng., 14(3):201-240 (1987).
Smith, et al., "Amidrazones III. The Synthesis And Properties of 1,1,1-Trimethyl-2-(N-Phenlbenzimidoyl)Hydrazinium Hydroxide Inner Salt—A Novel Ylid", Tetrahedron Lett. (1973) 3941-42.
Smith, et al., "The Thermal Breakdown of Diaryltetrazoles", J. Am. Chem. Soc. (1958) 80, 4647-54.
Treat, et al., "Liposome Encapsulated Doxorubicin Preliminary Results of Phase I and Phase II Trials", Liposomes in the Therapy of Infectious Diseases and Cancer, Lopez-Berestein, et al., eds., Alan R. Liss, Inc., New York, pp. 353-365 (1989).
Wolfe, et al., "Simple, Efficient Catalyst System For The Palladium-Catalyzed Amination of Aryl Chlorides, Bromides, and Triflates", J. Org. Chem. (2000) 65, 1158-74.

\* cited by examiner

4-SUBSTITUTED IMIDAZO[4,5-C]PYRIDINE ANTAGONISTS OF GONADOTROPIN RELEASING HORMONE RECEPTOR

This application claims the benefit of provisional application U.S. Ser. No. 60/654,560, filed Feb. 18, 2005, which is hereby incorporated by reference into the subject application in its entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

The present invention relates to Gonadotropin Releasing Hormone (GnRH, also known as Luteinizing Hormone Releasing Hormone) receptor antagonists.

BACKGROUND OF THE INVENTION

Gonadotropin Releasing Hormone is a decameric peptide released from the hypothalamus. In the anterior pituitary gland, GnRH activates the GnRH receptor. Activation of the GnRH receptor triggers the release of follicle stimulating hormone (FSH) and luteinizing hormone (LH). FSH and LH stimulate the biosynthesis and release of sex steroids in the gonads of both genders.

Typically, this stimulation and release is desirable, but certain GnRH-related disorders exist where it would be beneficial to prevent activation of the GnRH receptor. For example, inhibition of the GnRH receptor can lead to a large drop in sex steroid production, which in turn can alleviate sex hormone-related conditions such as prostate cancer, endometriosis, uterine fibroids, uterine cancer, breast cancer, ovarian cancer, testicular cancer, or primary hirsutism. Moreover, there are other situations where it would be beneficial to prevent activation of the GnRH receptor, such as during some points of the in vitro fertilization process, for example, to prevent LH surge.

Currently marketed GnRH therapeutics are peptides that exhibit receptor antagonism in one of two ways. The first is through GnRH receptor superagonism. The GnRH receptor, when stimulated in bursts, causes normal relase of the gonadotropins, FSH and LH. Under constant stimulation, the receptor becomes desensitized and the overall effect is GnRH receptor inhibition. The superagonism process is undesirable, because inhibition via this process can take up to two weeks to have an effect in human patients. During this delay, there is often an increase in disease symptoms due to the initial hormone stimulation phase. This phenomenon is referred to as flare.

The second method for receptor inhibition is through direct antagonism of the GnRH receptor with peptide antagonists. This causes an immediate drop in plasma LH levels. However, as mentioned above, current pharmaceuticals that cause blockade of the GnRH receptor are all peptides. As such they are not orally bioavailable and must be administered via parenteral means such as intravenous, subcutaneous, or intramuscular injection. Thus, an orally effective GnRH antagonist would be of great benefit.

The present invention is directed to these and other important ends.

SUMMARY OF THE INVENTION

In one embodiment, the invention provides compounds of the formula (I):

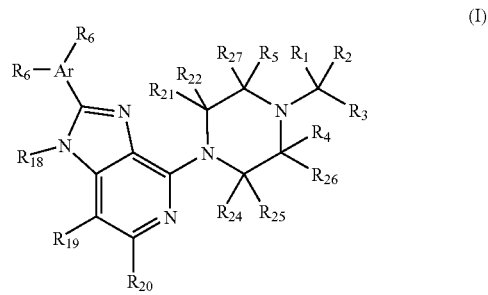

and pharmaceutically acceptable salts thereof,
wherein
Ar is phenyl, 2-thiophenyl or 3-thiophenyl;
$R^1$ and $R_2$ are each independently hydrogen; or linear or branched $(C_1-C_6)$-alkyl, $(C_2-C_6)$-alkenyl, or $(C_2-C_6)$ alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-CH_2)_nOR_{23}$;
$R_3$ is one of the following:

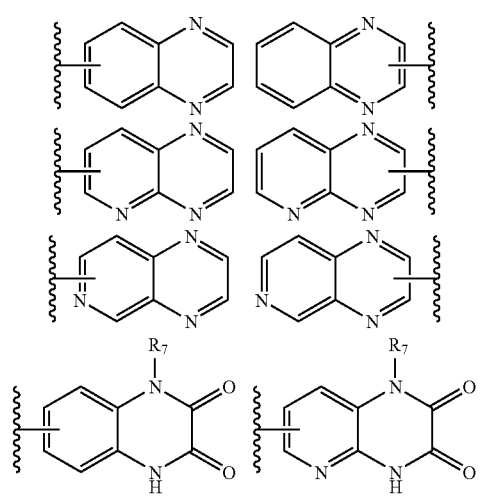

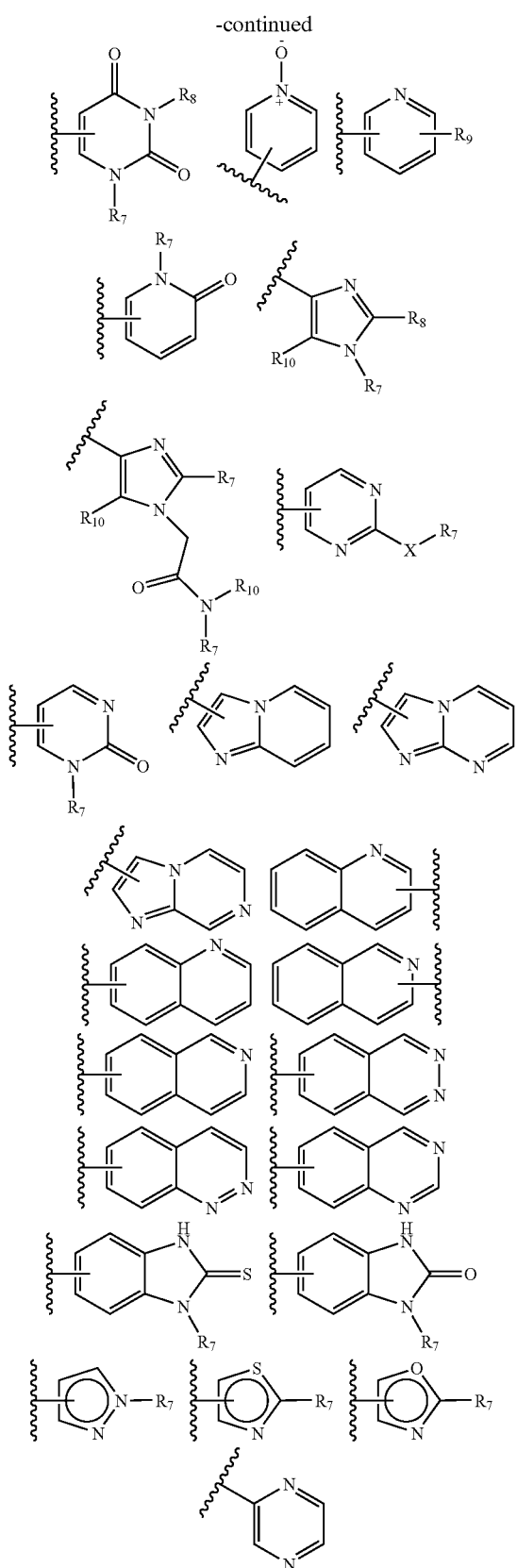

each R$_3$ also having up to three R$_{10}$ substituents attached to a ring of R$_3$ containing at least one N;

R$_4$, R$_5$, R$_{10}$, R$_{18}$, R$_{19}$, R$_{20}$, R$_{21}$, R$_{22}$, R$_{23}$, R$_{24}$, R$_{25}$, R$_{26}$, and R$_{27}$ are each independently hydrogen; or linear or branched (C$_1$-C$_6$)-alkyl, (C$_2$-C$_6$)-alkenyl, or (C$_2$-C$_6$)-alkynyl;

each R$_6$ is independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; —NR$_{13}$R$_{14}$; —C(OH)(CF$_3$)$_2$; —CH(CF$_3$)$_2$; C(CF$_3$)$_3$; —XR$_{13}$; or —COR$_{13}$; and when two R$_6$ are ortho to each other, they may together form a five- to seven-membered cyclic group containing up to 3 heteroatoms selected from N, O, or S, and wherein the cyclic group formed by the ortho R$_6$ groups is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_7$ and R$_9$ are each independently hydrogen; linear or branched (C$_1$-C$_6$)-alkyl, (C$_2$-C$_6$)-alkenyl, or (C$_2$-C$_6$)-alkynyl; —R$_{11}$XR$_{12}$; —(CH$_2$)$_n$R$_{17}$; —COXR$_{11}$; —XR$_{11}$; —CO$_2$R$_{11}$; or —CONR$_{11}$R$_{12}$;

R$_8$ is hydrogen; linear or branched (C$_1$-C$_6$)-alkyl, (C$_2$-C$_6$)-alkenyl, or (C$_2$-C$_6$)-alkynyl; —(CH$_2$)$_m$CO$_2$R$_{11}$; or —(CH$_2$)$_m$CONR$_{11}$R$_{12}$;

R$_{11}$ and R$_{12}$ are each independently hydrogen; linear or branched (C$_1$-C$_6$)-alkyl, (C$_2$-C$_6$)-alkenyl, or (C$_2$-C$_6$)-alkynyl; or R$_{11}$ and R$_{12}$ may together form a three- to seven-membered heterocyclic group containing up to 3 heteroatoms selected from N, O, or S;

R$_{13}$ and R$_{14}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —(CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

X is —O—, —NR$_{12}$—, or —SO$_m$—;

each m is independently 0, 1, or 2; and each n is independently 0, 1, 2, 3, or 4.

In another embodiment, the invention provides compounds of the formula (Ia):

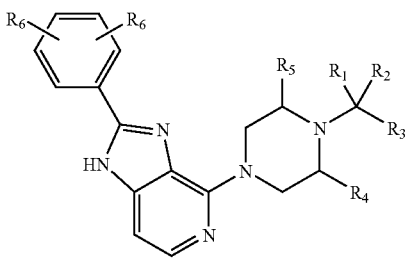

(Ia)

and pharmaceutically acceptable salts thereof, wherein each of $R_1$, $R_2$, $R_3$, $R_4$, $R_5$, and $R_6$ are as described above for compounds of the formula (I).

In another embodiment, the compounds or pharmaceutically acceptable salts of the compounds of Formula (I) or Formula (Ia) are useful as pharmaceutical compositions comprising compounds or pharmaceutically acceptable salts of compounds of Formula (I) or Formula (Ia) and a pharmaceutically acceptable carrier.

In one embodiment, the compounds or pharmaceutically acceptable salts of the compounds of the Formula (I) or Formula (Ia) are useful as GnRH receptor antagonists.

In one embodiment, the invention provides methods for treating a GnRH-related disorder, comprising administering to a mammal in need thereof the compounds or pharmaceutically acceptable salts of compounds of Formula (I) or Formula (Ia) in an amount effective to treat a GnRH-related disorder. In another embodiment, the invention provides methods for preventing pregnancy, comprising administering to a female mammal the compounds or pharmaceutically acceptable salts of compounds of the Formula (I) or Formula (Ia) in an amount effective to prevent pregnancy.

In one embodiment, the invention provides methods of synthesizing the compounds or pharmaceutically acceptable salts of compounds of Formula (I) or Formula (Ia). In another embodiment, the invention provides compounds or pharmaceutically acceptable salts of compounds of Formula (I) or Formula (Ia) made by particular processes.

DESCRIPTION OF THE INVENTION

Definitions

The term "$(C_1-C_6)$-alkyl" as used herein refers to a linear or branched, saturated hydrocarbon having from 1 to 6 carbon atoms. Representative $(C_1-C_6)$-alkyl groups include, but are not limited to, methyl, ethyl, propyl, isopropyl, butyl, sec-butyl, tert-butyl, pentyl, isopentyl, neopentyl, hexyl, isohexyl, and neohexyl. In one embodiment, the $(C_1-C_6)$-alkyl group is substituted with one or more of the following groups: halogen, —$N_3$, —$NO_2$, —CN, —OR', —SR', —$SO_2R'$, —$SO_2N(R')_2$, —$N(R')_2$, —COR', —$CO_2R'$, —NR'$CO_2R'$, —NR'COR', —NR'CONR', or —CON(R')$_2$, wherein each R' is independently hydrogen or unsubstituted $(C_1-C_6)$-alkyl.

The term "$(C_2-C_6)$-alkenyl" as used herein refers to a linear or branched hydrocarbon having from 2 to 6 carbon atoms and having at least one carbon-carbon double bond. In one embodiment, the $(C_2-C_6)$-alkenyl has one or two double bonds. The $(C_2-C_6)$-alkenyl moiety may exist in the E or Z conformation and the compounds of the present invention include both conformations. In one embodiment, the $(C_2-C_6)$-alkenyl group is substituted with one or more of the following groups: halogen, —$N_3$, —$NO_2$, —CN, —OR', —SR', —$SO_2R'$, —$SO_2N(R')_2$, —$N(R')_2$, —COR', —$CO_2R'$, —NR'$CO_2R'$, —NR'COR', —NR'CONR', or —CON(R')$_2$, wherein each R' is independently hydrogen or unsubstituted $(C_1-C_6)$-alkyl.

The term "$(C_2-C_6)$-alkynyl" as used herein refers to a linear or branched hydrocarbon having from 2 to 6 carbon atoms and having at least one carbon-carbon triple bond. In one embodiment, the $(C_2-C_6)$-alkenyl group is substituted with one or more of the following groups: halogen, —$N_3$, —$NO_2$, —CN, —OR', —SR', —$SO_2R'$, —$SO_2N(R')_2$, —$N(R')_2$, —COR', —$CO_2R'$, —NR'$CO_2R'$, —NR'COR', —NR'CONR', or —CON(R')$_2$, wherein each R' is independently hydrogen or unsubstituted $(C_1-C_6)$-alkyl.

The term "administer", "administering", or "administration", as used herein refers to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of active compound within the animal's body.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "amine protecting group" as used herein refers to a moiety that temporarily blocks an amine reactive site in a compound. Generally, this is done so that a chemical reaction can be carried out at another reactive site in a multifunctional compound or to otherwise stabilize the amine. In one embodiment, an amine protecting group is selectively removable by a chemical reaction. An exemplary amine protecting group is a carbamate protecting group. Carbamate protecting groups include, without limitation, t-butyl carbamate, methyl carbamate, ethyl carbamate, 2,2,2-trichloroethyl carbamate, 2-(trimethylsilyl)ethyl carbamate, 1,1-dimethyl-2,2,2-trichloroethyl carbamate, benzyl carbamate, p-methoxybenzyl carbamate, p-nitrobenzylcarbamate, p-bromobenzyl carbamate, p-chlorobenzyl carbamate, and 2,4-dichlorobenzyl carbamate. See, Greene and Wuts, *Protecting Groups in Organic Synthesis*, Second Edition, John Wiley & Sons (1991).

The term "aryl" as used herein refers to an aromatic species containing 1 to 3 aromatic rings, either fused or linked. In one embodiment, the aryl group is substituted with one or more of the following groups: $(C_1-C_6)$-alkyl, -V-halogen, -V-$N_3$, -V-$NO_2$, -V-CN, -V-OR', -V-SR', -V-$SO_2R'$, -V-$SO_2N(R')_2$, -V-N(R')$_2$, -V-COR', -V-$CO_2R'$, -V-NR'$CO_2R'$, -V-NR'COR', -V-NR'CONR', or -V-CON(R')$_2$, wherein each R' is independently hydrogen or unsubstituted $(C_1-C_6)$-alkyl; and wherein each V is independently a bond or $(C_1-C_6)$-alkyl.

The term "conditions effective to" as used herein refers to synthetic reaction conditions which will be apparent to those skilled in the art of synthetic organic chemistry.

The term "cyclic group" as used herein includes a cycloalkyl group and a heterocyclic group. Any suitable ring position of the cyclic group may be covalently linked to the defined chemical structure. In one embodiment, the cyclic group is substituted with one or more of the following groups: $(C_1-C_6)$-alkyl, -V-halogen, -V-$N_3$, -V-$NO_2$, -V-CN, -V-OR', -V-SR', -V-$SO_2R'$, -V-$SO_2N(R')_2$, -V-N(R')$_2$, -V-COR', -V-$CO_2R'$, -V-NR'$CO_2R'$, -V-NR'COR', -V-NR'CONR', or -V-CON(R')$_2$, wherein each R' is independently hydrogen or unsubstituted $(C_1-C_6)$-alkyl; and wherein each V is independently a bond or $(C_1-C_6)$-alkyl.

The term "cycloalkyl group" as used herein refers to a three- to seven-membered saturated or partially unsaturated carbon ring. Any suitable ring position of the cycloalkyl group may be covalently linked to the defined chemical structure. Exemplary cycloalkyl groups include cyclopropyl, cyclobutyl, cyclopentyl, cyclohexyl, and cycloheptyl. In one embodiment, the cycloalkyl group is substituted with one or more of the following groups: $(C_1-C_6)$-alkyl, -V-halogen, -V-$N_3$, -V-$NO_2$, -V-CN, -V-OR', -V-SR', -V-$SO_2$R', -V-$SO_2$N(R')$_2$, -V-N(R')$_2$, -V-COR', -V-$CO_2$R', -V-NR'$CO_2$R', -V-NR'COR', -V-NR'CONR', or -V-CON(R')$_2$, wherein each R' is independently hydrogen or unsubstituted $(C_1-C_6)$-alkyl; and wherein each V is independently a bond or $(C_1-C_6)$-alkyl.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "FSH" as used herein refers to follicle stimulating hormone.

The term "GnRH" as used herein refers to Gonadotropin Releasing Hormone.

The term "Gonadotropin Releasing Hormone-related disorder" or "GnRH-related disorder" as used herein refers to a condition for which it would be beneficial to prevent activation of the GnRH receptor. Exemplary GnRH-related disorders include, without limitation, sex hormone-related conditions, sex hormone-dependent cancers, prostate cancer, testicular cancer, uterine cancer, ovarian cancer, breast cancer, pituitary gonadotrophe adenomas, endometriosis, polycystic ovarian disease, uterine fibroids, primary hirsuitsm, luteinizing hormone surge, and precocious puberty.

The term "LH" as used herein refers to luteinizing hormone.

The term "halogen" as used herein refers to fluorine, chlorine, bromine, and iodine.

The term "heterocyclic group" as used herein refers to a three- to seven-membered saturated, partially saturated, or unsaturated cycloalkyl group in which one to four of the ring carbon atoms have been independently replaced with a N, O, or S atom. Any suitable ring position of the heterocyclic group may be covalently linked to the defined chemical structure. Exemplary heterocyclic groups include, but are not limited to, azepanyl, azetidinyl, aziridinyl, furanyl, furazanyl, homopiperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. In one embodiment, the heterocyclic group is substituted with one or more of the following groups: $(C_1-C_6)$-alkyl, -V-halogen, -V-$N_3$, -V-$NO_2$, -V-CN, -V-OR', -V-SR', -V-$SO_2$R', -V-$SO_2$N(R')$_2$, -V-N(R')$_2$, -V-COR', -V-$CO_2$R', -V-NR'$CO_2$R', -V-NR'COR', -V-NR'CONR', or -V-CON(R')$_2$, wherein each R' is independently hydrogen or unsubstituted $(C_1-C_6)$-alkyl; and wherein each V is independently a bond or $(C_1-C_6)$-alkyl.

The term "isolated and purified" as used herein refers to separate from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—$(C_1-C_6)$-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "phenyl" as used herein refers to a substituted or unsubstituted phenyl group. In one embodiment, the phenyl group is substituted with one or more of the following groups: $(C_1-C_6)$-alkyl, -V-halogen, -V-$N_3$, -V-$NO_2$, -V-CN, -V-OR', -V-SR', -V-$SO_2$R', -V-$SO_2$N(R')$_2$, -V-N(R')$_2$, -V-COR', -V-$CO_2$R', -V-NR'$CO_2$R', -V-NR'COR', -V-NR'CONR', or -V-CON(R')$_2$, wherein each R' is independently hydrogen or unsubstituted $(C_1-C_6)$-alkyl; and wherein each V is independently a bond or $(C_1-C_6)$-alkyl.

The term "substantially free of its corresponding opposite enantiomer" as used herein means that the compound contains no more than about 10% by weight of its corresponding opposite enantiomer. In other embodiments, the compound that is substantially free of its corresponding opposite entantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

Compounds and Pharmaceutically Acceptable Salts of Compounds of the Invention

In one embodiment, the present invention is directed to compounds of the Formula (I):

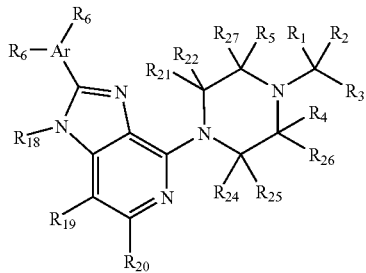

(I)

and pharmaceutically acceptable salts thereof,
wherein

Ar is phenyl, 2-thiophenyl or 3-thiophenyl;

$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_3$ is one of the following:

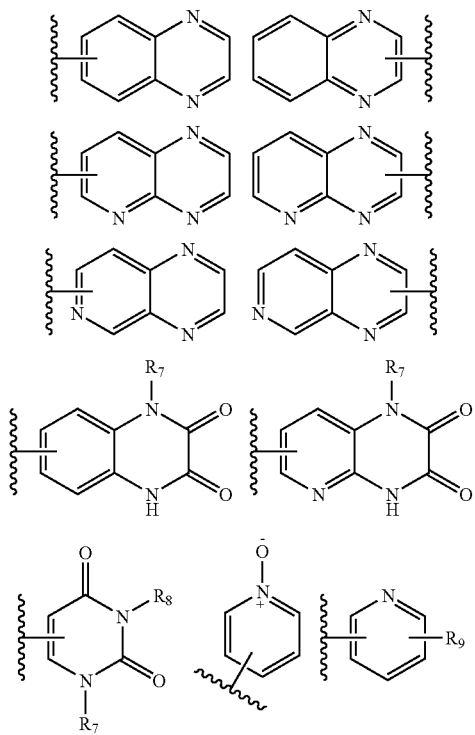

-continued

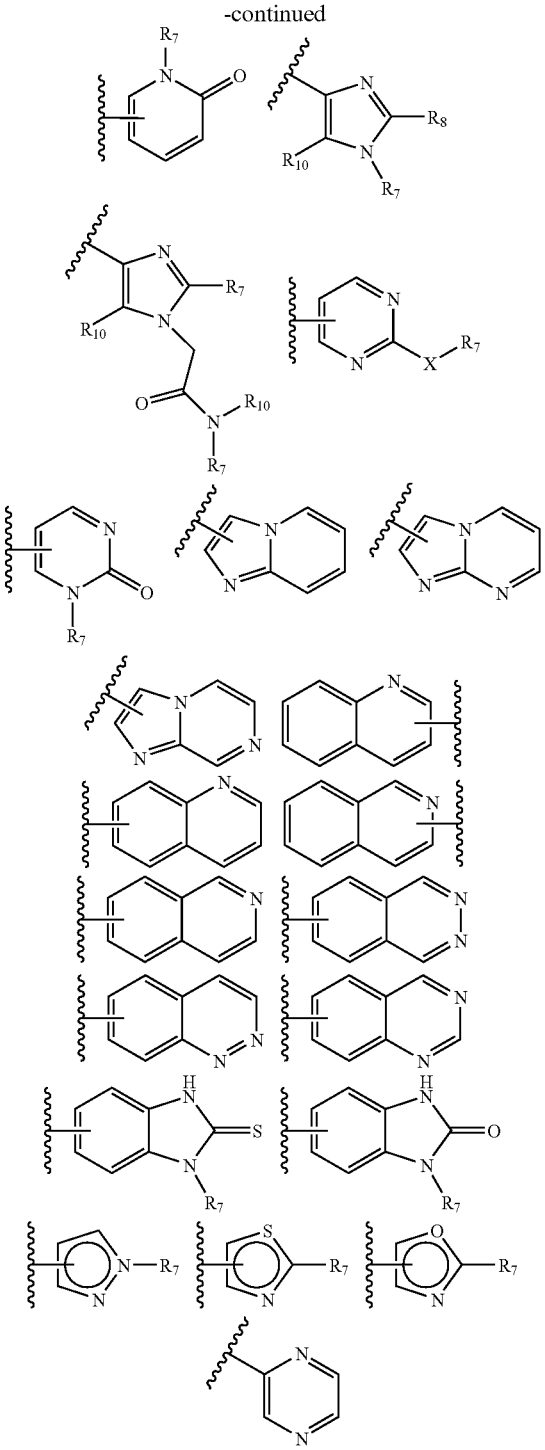

each $R_3$ also having up to three $R_{10}$ substituents attached to a ring of $R_3$ containing at least one N;

$R_4$, $R_5$, $R_{10}$, $R_{18}$, $R_{19}$, $R_{20}$, $R_{21}$, $R_{22}$, $R_{23}$, $R_{24}$, $R_{25}$, $R_{26}$, and $R_{27}$ are each independently hydrogen; or linear or branched $(C_1-C_6)$-alkyl, $(C_2-C_6)$-alkenyl, or $(C_2-C_6)$-alkynyl;

each $R_6$ is independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; —NR$_{13}$R$_{14}$; —C(OH)(CF$_3$)$_2$; —CH(CF$_3$)$_2$; C(CF$_3$)$_3$; —XR$_{13}$; or —COR$_{13}$; and when two R$_6$ are ortho to each other, they may together form a five- to seven-membered cyclic group containing up to 3 heteroatoms selected from N, O, or S, and wherein the cyclic group formed by the ortho R$_6$ groups is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2$)$_n$OR$_{23}$;

R$_7$ and R$_9$ are each independently hydrogen; linear or branched (C$_1$-C$_6$)-alkyl, (C$_2$-C$_6$)-alkenyl, or (C$_2$-C$_6$)-alkynyl; —R$_{11}$XR$_{12}$; —(CH$_2$)$_n$R$_{17}$; —COXR$_{11}$; —XR$_{11}$; —CO$_2$R$_{11}$; or —CONR$_{11}$R$_{12}$;

R$_8$ is hydrogen; linear or branched (C$_1$-C$_6$)-alkyl, (C$_2$-C$_6$)-alkenyl, or (C$_2$-C$_6$)-alkynyl; —(CH$_2$)$_m$CO$_2$R$_{11}$; or —(CH$_2$)$_m$CONR$_{11}$R$_{12}$;

R$_{11}$ and R$_{12}$ are each independently hydrogen; linear or branched (C$_1$-C$_6$)-alkyl, (C$_2$-C$_6$)-alkenyl, or (C$_2$-C$_6$)-alkynyl; or R$_{11}$ and R$_{12}$ may together form a three- to seven-membered heterocyclic group containing up to 3 heteroatoms selected from N, O, or S;

R$_{13}$ and R$_{14}$ are each independently hydrogen; linear or branched (C$_1$-C$_6$)-alkyl, (C$_2$-C$_6$)-alkenyl, or (C$_2$-C$_6$) alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

X is —O—, —NR$_{12}$—, or —SO$_m$—;

each m is independently 0, 1, or 2; and each n is independently 0, 1, 2, 3, or 4.

In one embodiment, Ar is phenyl.

In another embodiment, one R$_6$ substituent is attached at the 4 position of phenyl.

In one embodiment, R$_1$ and R$_2$ are each independently hydrogen; linear or branched (C$_1$-C$_6$)-alkyl; or R$_1$ and R$_2$ may together form a three- to seven-membered cycloalkyl group.

In another embodiment, R$_1$ and R$_2$ are hydrogen.

In one embodiment, R$_1$ is linear or branched (C$_1$-C$_6$)-alkyl and R$_2$ is hydrogen.

In one embodiment, R$_1$ is methyl and R$_2$ is hydrogen.

In one embodiment, when R$_1$ and R$_2$ are different, the compound or pharmaceutically acceptable salt of the compound is the S-enantiomer with respect to the carbon to which R$_1$ and R$_2$ are bound.

In another embodiment, when R$_1$ and R$_2$ are different, the compound or pharmaceutically acceptable salt of the compound is the R-enantiomer with respect to the carbon to which R$_1$ and R$_2$ are bound.

In one embodiment, R$_4$ and R$_5$ are each independently hydrogen, or linear or branched (C$_1$-C$_6$)-alkyl.

In one embodiment, R$_4$ and R$_5$ are hydrogen.

In another embodiment, R$_4$ is linear or branched (C$_1$-C$_6$)-alkyl and R$_5$ is hydrogen.

In one embodiment, R$_4$ is methyl or ethyl and R$_5$ is hydrogen.

In another embodiment, when R$_4$ is other than hydrogen, the compound or pharmaceutically acceptable salt of the compound is the S-enantiomer with respect to the carbon to which R$_4$ is bound.

In one embodiment, when R$_1$ and R$_2$ are different, the compound or pharmaceutically acceptable salt of the compound is the S-enantiomer with respect to the carbon to which R$_1$ and R$_2$ are bound, and when R$_4$ is other than hydrogen, the compound or pharmaceutically acceptable salt of the compound is the S-enantiomer with respect to the carbon to which R$_4$ is bound.

In another embodiment, when R$_1$ and R$_2$ are different, the compound or pharmaceutically acceptable salt of the compound is the R-enantiomer with respect to the carbon to which R$_1$ and R$_2$ are bound, and when R$_4$ is other than hydrogen, the compound or pharmaceutically acceptable salt of the compound is the S-enantiomer with respect to the carbon to which R$_4$ is bound.

In one embodiment, R$_6$ is hydrogen, linear or branched (C$_1$-C$_6$)-alkyl, —N(R$_{23}$)$_2$, or —NR$_{13}$R$_{14}$; R$_{23}$ is linear or branched (C$_1$-C$_6$)-alkyl; and R$_{13}$ and R$_{14}$ are each independently linear or branched (C$_1$-C$_6$)-alkyl, each optionally substituted with —OR$_{23}$, —SR$_{23}$, or —N(R$_{23}$)$_2$; or R$_{13}$ and R$_{14}$ may be taken together to form a three- to seven-membered heterocyclic group containing one or two heteroatoms selected from N or O, and optionally substituted with —OR$_{23}$, —SR$_{23}$, —N(R$_{23}$)$_2$, or —CH$_2$)$_n$OR$_{23}$.

In one embodiment, R$_6$ is ethyl, t-butyl, —N(CH$_2$CH$_3$)$_2$, pyrrolidine, 2-hydroxymethylpyrrolidine, or isopropyl.

In one embodiment, R$_3$ is

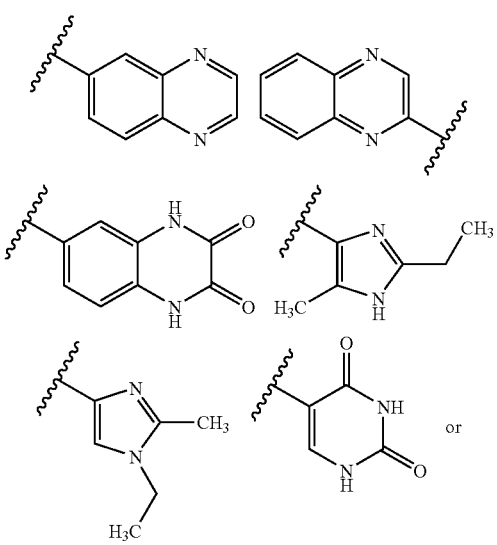

-continued

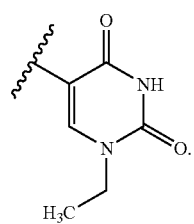

In another embodiment, $R_3$ is

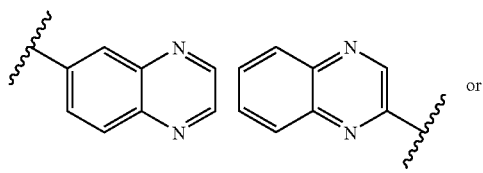

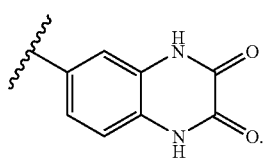

In one embodiment, $R_{18}$, $R_{19}$, $R_{20}$, $R_{21}$, $R_{22}$, $R_{24}$, $R_{25}$, $R_{26}$, and $R_{27}$ are each independently hydrogen, or linear or branched ($C_1$-$C_6$)-alkyl.

In another embodiment, $R_{18}$, $R_{19}$, $R_{20}$, $R_{21}$, $R_{22}$, $R_{24}$, $R_{25}$, $R_{26}$, and $R_{27}$ are each hydrogen.

In one embodiment, $R_{18}$, $R_{19}$, $R_{20}$, $R_{21}$, $R_{22}$, $R_{24}$, $R_{25}$, $R_{26}$, and $R_{27}$ are each hydrogen; $R_1$, $R_2$, $R_4$, and $R_5$ are each independently hydrogen, or linear or branched ($C_1$-$C_6$)-alkyl; Ar is phenyl; $R_6$ is attached at the 4-position of phenyl; $R_6$ is linear or branched ($C_1$-$C_6$)-alkyl, —N($R_{23}$)$_2$, or —N$R_{13}R_{14}$; $R_{23}$ is linear or branched ($C_1$-$C_6$)-alkyl; $R_{13}$ and $R_{14}$ are each independently linear or branched ($C_1$-$C_6$)-alkyl, each optionally substituted with —O$R_{23}$, —S$R_{23}$, or —N($R_{23}$)$_2$; or $R_{13}$ and $R_{14}$ may be taken together to form a three- to seven-membered heterocyclic group containing one or two heteroatoms selected from N or O, and optionally substituted with —O$R_{23}$, —S$R_{23}$, —N($R_{23}$)$_2$, or —(CH$_2$)$_n$O$R_{23}$; and $R_3$ is

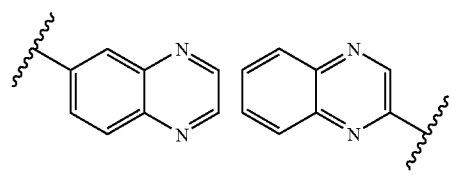

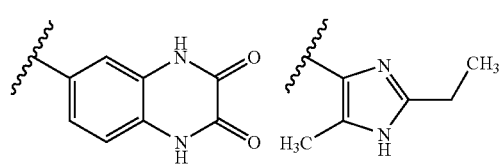

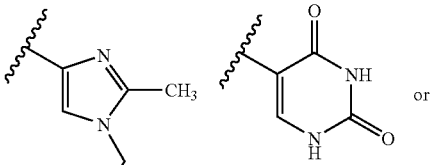

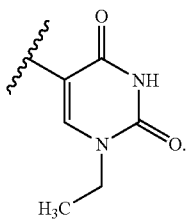

In one embodiment, $R_2$, $R_5$, $R_{18}$, $R_{19}$, $R_{20}$, $R_{21}$, $R_{22}$, $R_{24}$, $R_{25}$, $R_{26}$, and $R_{27}$ are each hydrogen; $R_1$ and $R_4$ are each independently hydrogen, methyl, or ethyl; Ar is phenyl; $R_6$ is attached at the 4-position of phenyl; $R_6$ is ethyl, t-butyl, —N(CH$_2$CH$_3$)$_2$, pyrrolidine, 2-hydroxymethylpyrrolidine, or isopropyl; and $R_3$ is

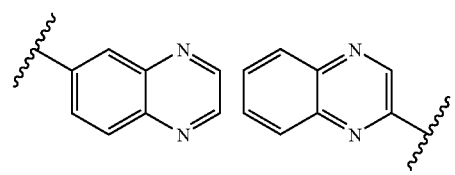

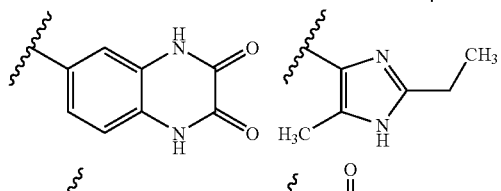

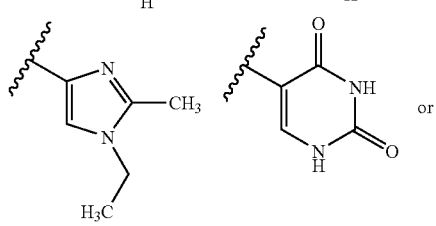

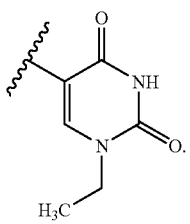

In one embodiment, the compound is 6-{4-[2-(4-tert-butyl-phenyl)-1H-imidazo[4,5-c]pyridin-4-yl]-piperazin-1-ylmethyl}quinoxaline; 6-{4-[2-(4-tert-butyl-phenyl)-1H-imidazo[4,5-c]pyridin-4-yl]-piperazin-1-ylmethyl}-1,4-dihydroquinoxaline-2,3-dione; 2-{4-[2-(4-tert-butyl-phenyl)-1H-imidazo[4,5-c]pyridin-4-yl]-piperazin-1-ylmethyl}-quinoxaline; 2-(4-tert-butyl-phenyl)-4-[4-(2-ethyl-5-methyl-1H-imidazol-4-ylmethyl)-piperazin-1-yl]-1H-imidazo[4,5-c]pyridine; 2-(4-tert-butyl-phenyl)-4-[4-(1, 2-dimethyl-1H-imidazol-4-ylmethyl)-piperazin-1-yl]-1H-imidazo[4,5-c]pyridine; 5-{4-[2-(4-tert-butyl-phenyl)-1H-imidazo[4,5-c]pyridin-4-yl]-piperazin-1-ylmethyl}-1H-pyrimidine-2,4-dione; or 5-{4-[2-(4-tert-butyl-phenyl)-1H-imidazo[4,5-c]pyridin-4-yl]-piperazin-1-ylmethyl}-1-ethyl-1H-pyrimidine-2,4-dione.

In another embodiment, the invention provides compounds of the Formula (Ia):

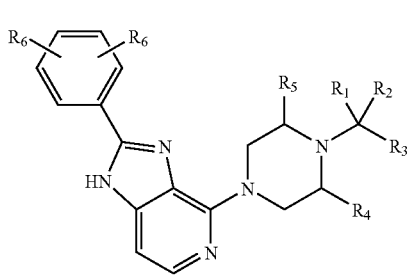

(Ia)

and pharmaceutically acceptable salts thereof,
wherein
R$_1$ and R$_2$ are each independently hydrogen; or linear or branched (C$_1$-C$_6$)-alkyl, (C$_2$-C$_6$)-alkenyl, or (C$_2$-C$_6$) alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; or R$_1$ and R$_2$ may together form a three- to seven-membered cycloalkyl group, wherein the cycloalkyl group formed by R$_1$ and R$_2$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2)_n$OR$_{23}$;
R$_3$ is one of the following:

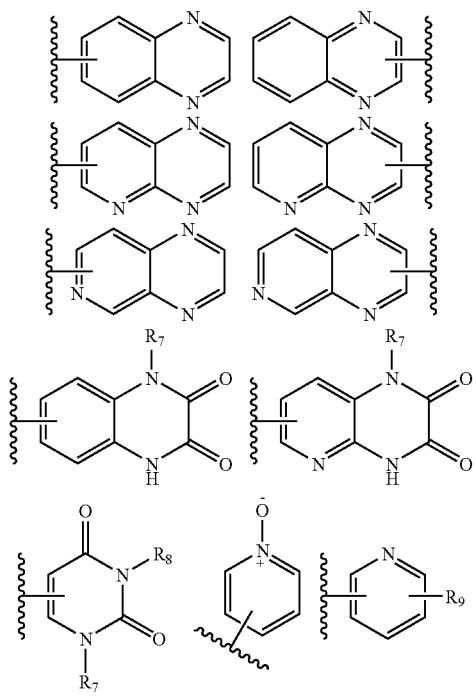

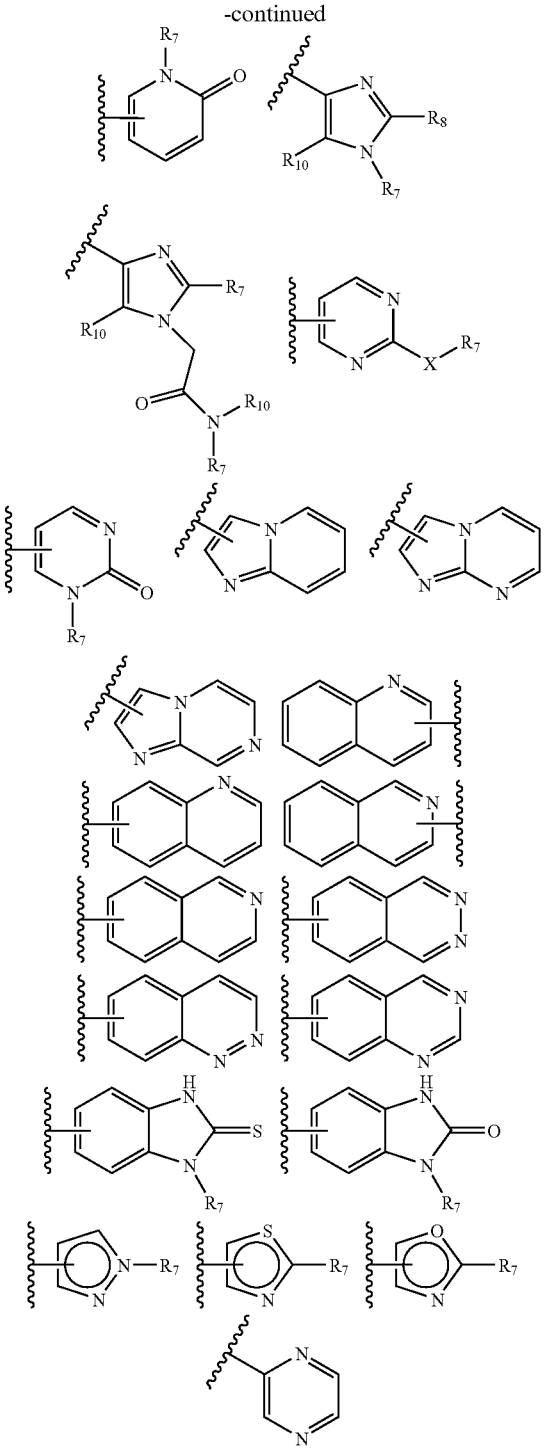

each R$_3$ also having up to three R$_{10}$ substituents attached to a ring of R$_3$ containing at least one N;
R$_4$, R$_5$, R$_{10}$, and R$_{23}$ are each independently hydrogen; or linear or branched (C$_1$-C$_6$)-alkyl, (C$_2$-C$_6$)-alkenyl, or (C$_2$-C$_6$)-alkynyl;
each R$_6$ is independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; —NR$_{13}$R$_{14}$; —C(OH)(CF$_3$)$_2$; —CH(CF$_3$)$_2$; —C(CF$_3$)$_3$; —XR$_{13}$; or —COR$_{13}$; and when two R$_6$ are ortho to each other, they may together form a five- to seven-membered cyclic group containing up to 3 heteroatoms selected from N, O, or S, and wherein the cyclic group formed by the ortho R$_6$ groups is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2$)$_n$OR$_{23}$;

R$_7$ and R$_9$ are each independently hydrogen; linear or branched (C$_1$-C$_6$)-alkyl, (C$_2$-C$_6$)-alkenyl, or (C$_2$-C$_6$)-alkynyl; R$_{11}$XR$_{12}$; —(CH$_2$)$_n$R$_{17}$; —COXR$_{11}$; —XR$_{11}$; —CO$_2$R$_{11}$; or —CONR$_{11}$R$_{12}$;

R$_8$ is hydrogen; linear or branched (C$_1$-C$_6$)-alkyl, (C$_2$-C$_6$)-alkenyl, or (C$_2$-C$_6$)-alkynyl; —(CH$_2$)$_m$CO$_2$R$_{11}$; or —(CH$_2$)$_m$CONR$_{11}$R$_{12}$;

R$_{11}$ and R$_{12}$ are each independently hydrogen; linear or branched (C$_1$-C$_6$)-alkyl, (C$_2$-C$_6$)-alkenyl, or (C$_2$-C$_6$)-alkynyl; or R$_{11}$ and R$_{12}$ may together form a three- to seven-membered heterocyclic group containing up to 3 heteroatoms selected from N, O, or S;

R$_{13}$ and R$_{14}$ are each independently hydrogen; linear or branched (C$_1$-C$_6$)-alkyl, (C$_2$-C$_6$)-alkenyl, or (C$_2$-C$_6$)-alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

X is —O—, —NR$_{12}$—, or —SO$_m$—;

each m is independently 0, 1, or 2; and each n is independently 0, 1, 2, 3, or 4.

In one embodiment, one R$_6$ substituent is attached at the 4 position of phenyl.

In one embodiment, R$_1$ and R$_2$ are each independently hydrogen; linear or branched (C$_1$-C$_6$)-alkyl; or R$_1$ and R$_2$ may together form a three- to seven-membered cyclic group.

In another embodiment, R$_1$ and R$_2$ are hydrogen.

In one embodiment, R$_1$ is linear or branched (C$_1$-C$_6$)-alkyl and R$_2$ is hydrogen.

In one embodiment, R$_1$ is methyl and R$_2$ is hydrogen.

In one embodiment, when R$_1$ and R$_2$ are different, the compound or pharmaceutically acceptable salt of the compound is the S-enantiomer with respect to the carbon to which R$_1$ and R$_2$ are bound.

In another embodiment, when R$_1$ and R$_2$ are different, the compound or pharmaceutically acceptable salt of the compound is the R-enantiomer with respect to the carbon to which R$_1$ and R$_2$ are bound.

In one embodiment, R$_4$ and R$_5$ are each independently hydrogen, or linear or branched (C$_1$-C$_6$)-alkyl.

In one embodiment, R$_4$ and R$_5$ are hydrogen.

In another embodiment, R$_4$ is linear or branched (C$_1$-C$_6$)-alkyl and R$_5$ is hydrogen.

In one embodiment, R$_4$ is methyl or ethyl and R$_5$ is hydrogen.

In another embodiment, when R$_4$ is other than hydrogen, the compound or pharmaceutically acceptable salt of the compound is the S-enantiomer with respect to the carbon to which R$_4$ is bound.

In one embodiment, when R$_1$ and R$_2$ are different, the compound or pharmaceutically acceptable salt of the compound is the S-enantiomer with respect to the carbon to which R$_1$ and R$_2$ are bound, and when R$_4$ is other than hydrogen, the compound or pharmaceutically acceptable salt of the compound is the S-enantiomer with respect to the carbon to which R$_4$ is bound.

In another embodiment, when R$_1$ and R$_2$ are different, the compound or pharmaceutically acceptable salt of the compound is the R-enantiomer with respect to the carbon to which R$_1$ and R$_2$ are bound, and when R$_4$ is other than hydrogen, the compound or pharmaceutically acceptable salt of the compound is the S-enantiomer with respect to the carbon to which R$_4$ is bound.

In one embodiment, R$_6$ is hydrogen, linear or branched (C$_1$-C$_6$)-alkyl, —N(R$_{23}$)$_2$, or —NR$_{13}$R$_{14}$; R$_{23}$ is linear or branched (C$_1$-C$_6$)-alkyl; and R$_{13}$ and R$_{14}$ are each independently linear or branched (C$_1$-C$_6$)-alkyl, each optionally substituted with —OR$_{23}$, —SR$_{23}$, or —N(R$_{23}$)$_2$; or R$_{13}$ and R$_{14}$ may be taken together to form a three- to seven-membered heterocyclic group containing one or two heteroatoms selected from N or O, and optionally substituted with —OR$_{23}$, —SR$_{23}$, —N(R$_{23}$)$_2$, or —(CH$_2$)$_n$OR$_{23}$.

In one embodiment, R$_6$ is ethyl, t-butyl, —N(CH$_2$CH$_3$)$_2$, pyrrolidine, 2-hydroxymethylpyrrolidine, or isopropyl.

In one embodiment, R$_3$ is

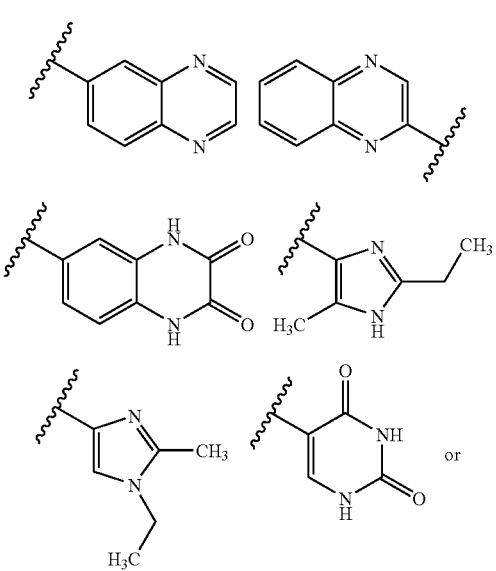

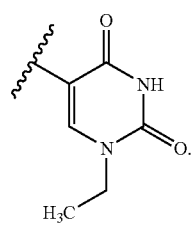

In another embodiment, $R_3$ is

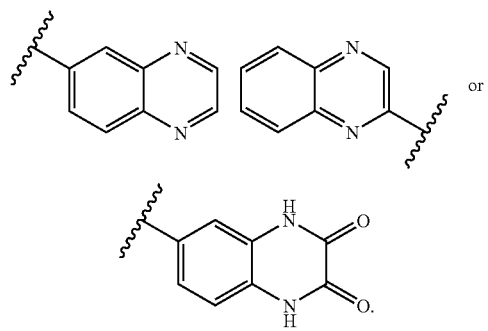

In one embodiment, $R_1$, $R_2$, $R_4$, and $R_5$ are each independently hydrogen, or linear or branched ($C_1$-$C_6$)-alkyl; & is attached at the 4-position of phenyl; $R_6$ is linear or branched ($C_1$-$C_6$)-alkyl, —N($R_{23}$)$_2$, or —NR$_{13}$R$_{14}$; $R_{23}$ is linear or branched ($C_1$-$C_6$)-alkyl; $R_{13}$ and $R_{14}$ are each independently linear or branched ($C_1$-$C_6$)-alkyl, each optionally substituted with —OR$_{23}$, —SR$_{23}$, or —N($R_{23}$)$_2$; or $R_{13}$ and $R_{14}$ may be taken together to form a three- to seven-membered heterocyclic group containing one or two heteroatoms selected from N or O, and optionally substituted with —OR$_{23}$, —SR$_{23}$, —N($R_{23}$)$_2$, or —(CH$_2$)$_n$OR$_{23}$; and $R_3$ is

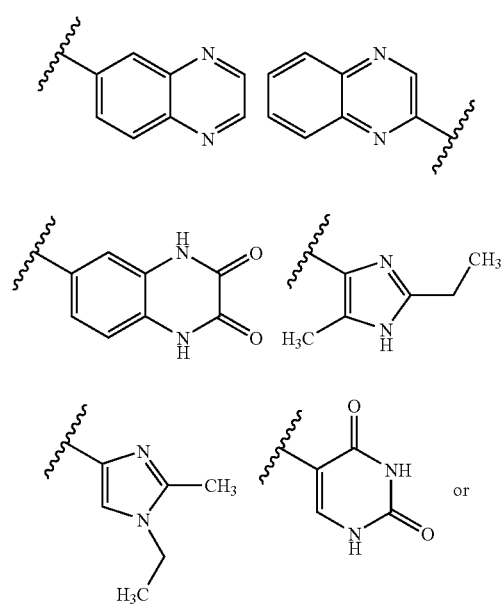

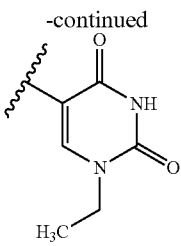

In one embodiment, $R_2$, and $R_5$ are each hydrogen; $R_1$ and $R_4$ are each independently hydrogen, methyl, or ethyl; $R_6$ is attached at the 4-position of phenyl; $R_6$ is ethyl, t-butyl, —N(CH$_2$CH$_3$)$_2$, pyrrolidine, 2-hydroxymethylpyrrolidine, or isopropyl; and $R_3$ is

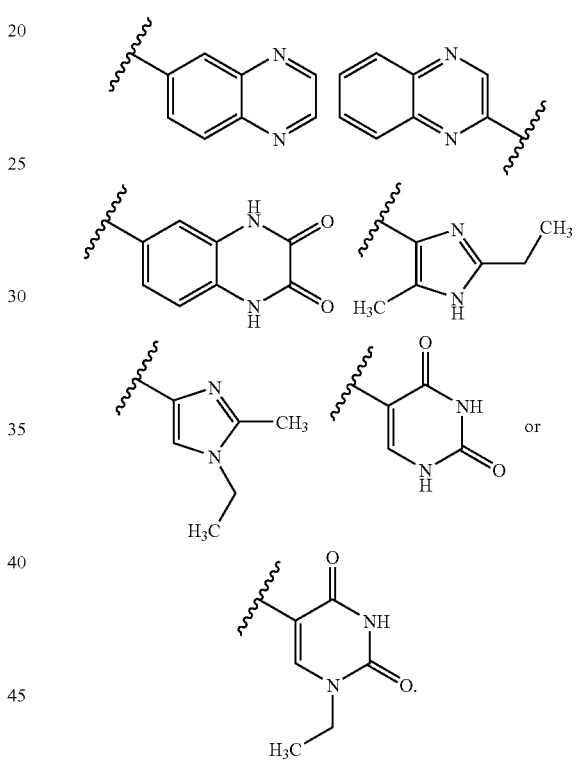

The compounds or pharmaceutically acceptable salts of compounds of the present invention can contain an asymmetric carbon atom and some of the compounds or pharmaceutically acceptable salts of compounds of the invention can contain one or more asymmetric centers, and can thus give rise to optical isomers and diastereomers. While depicted without respect to stereochemistry in the compounds or pharmaceutically acceptable salts of compounds of the present invention, the present invention includes such optical isomers and diastereomers, as well as racemic and resolved, enantiomerically pure R and S stereoisomers, and also other mixtures of the R and S stereoisomers and pharmaceutically acceptable salts thereof. Where a stereoisomer is preferred, it can in some embodiments be provided substantially free of its corresponding opposite enantiomer.

In addition, the compounds and pharmaceutically acceptable salts of compounds of the present invention can exist as tautomers. Such tautomers can be transient or isolatable as a stable product. These tautomers are within the scope of the present invention. For example, tautomerization of the compounds of Formula (I) can result in compounds of the Formula (I'):

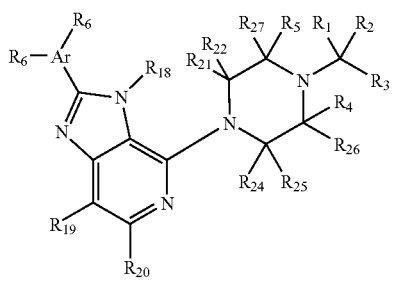

(I')

and pharmaceutically acceptable salts thereof, wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as set forth above for the compounds and pharmaceutically acceptable salts of compounds of Formula (I).

Prodrugs of the compounds or pharmaceutically acceptable salts of compounds are also within the scope of the present invention.

Methods for Making the Compounds and Pharmaceutically Acceptable Salts of Compounds of the Invention The compounds and pharmaceutically acceptable salts of compounds of the present invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecule.

The compounds and pharmaceutically acceptable salts of compounds of the present invention can be made generally according to the procedure provided in *J. Med. Chem.* 1990, 33 (8), 2231-2239, or by using the synthetic procedures outlined below in Schemes 1-4.

Scheme 1 demonstrates the production of a compound or pharmaceutically acceptable salt of a compound of the Formula (I), wherein Ar, $R_1$, $R_2$, $R_3$, $R_4$, $R_5$, $R_6$, $R_{18}$, $R_{19}$, $R_{20}$, $R_{21}$, $R_{22}$, $R_{24}$, $R_{25}$, $R_{26}$, and $R_{27}$ are as defined above and PG is hydrogen or an amine protecting group. A compound of the formula (II) is first treated with an aryl acid under conditions effective to bring about cyclization, thereby providing an imidazo[4,5-c]pyridine having the formula (III). The imidazo [4,5-c]pyridine of formula (III) is then treated under conditions effective to bring about chlorination, thereby providing a 4-chloro-imidazo[4,5-c]pyridine having the Formula (IV), which is reacted with a piperazine under conditions effective to produce a 4-piperazine-imidazo[4,5-c]pyridine having the formula (V). The free amine of the 4-piperazine-imidazo[4,5-c]pyridine of the formula (V) is subsequently reacted under conditions effective to provide the compound (I).

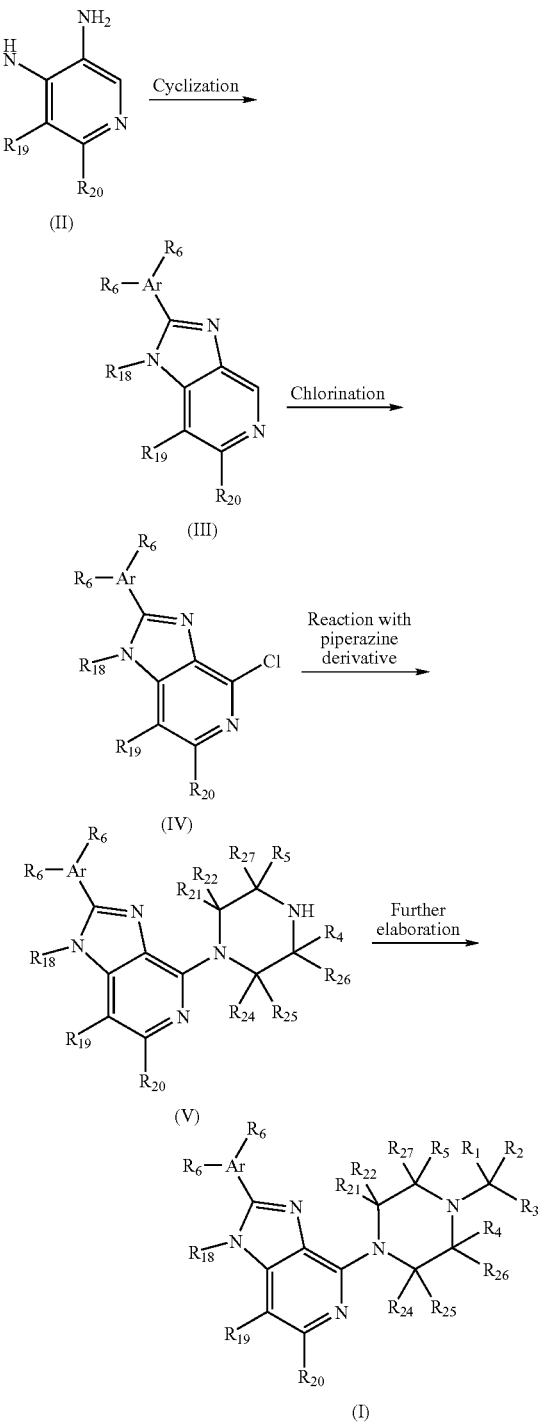

Scheme 2 demonstrates the production of a compound or pharmaceutically acceptable salt of a compound of Formula (I) having particular $R_1$, $R_2$, and $R_3$ groups. As shown in Scheme 2, a compound of Formula (V) can be reacted with 4-fluoro-3-nitrobenzylbromide under conditions effective to produce a compound of the Formula (VI). The compound of Formula (VI) is then treated under conditions effective to produce a diamine of the Formula (VII), which can be reacted under conditions effective to produce a compound of the Formula (VIII) or the Formula (IX).

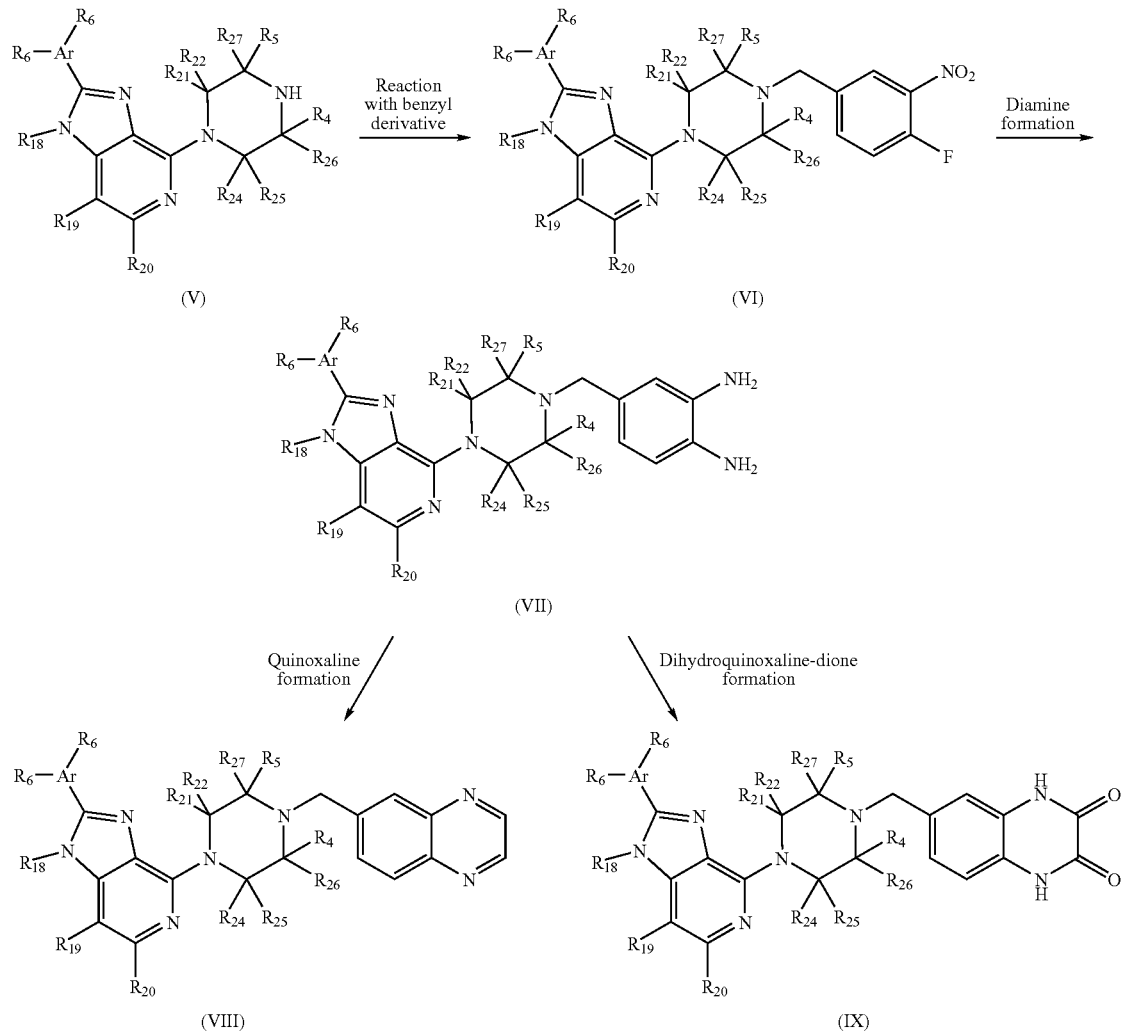

Schemes 3-4 demonstrate the synthetic methodology used to prepare particular compounds of the present invention.

The intermediate 5 is synthesized as shown in Scheme 3. 3,4-Diaminopyridine 1 and 4-t-butylbenzoic acid 2 are condensed and the product amide is cyclised to the imidazopyridine 3 through the addition of acetic acid followed by heating. The intermediate 3 is oxidized with mCPBA and the product is treated with hot phosphorous oxychloride to give 4. The chloride of 4 can be substituted by heating it with a large excess of piperidine in DMSO to provide 5.

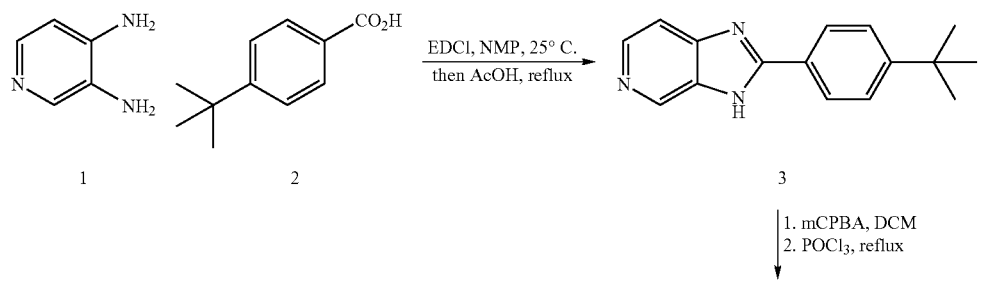

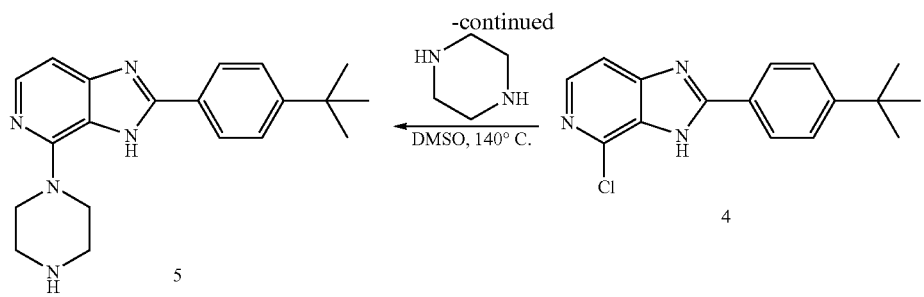
Scheme 4 first shows the preparation of the advanced intermediate 8. Piperazine 5 is treated with 4-fluoro-3-nitrobenzylbromide to provide 6, which is further elaborated by treatment with sodium azide in warm DMSO to provide 7. 7 is then catalytically reduced to 8. Substitution of the phenylenediamine portion of 8 provided the target products 2 and 10.
Scheme 4
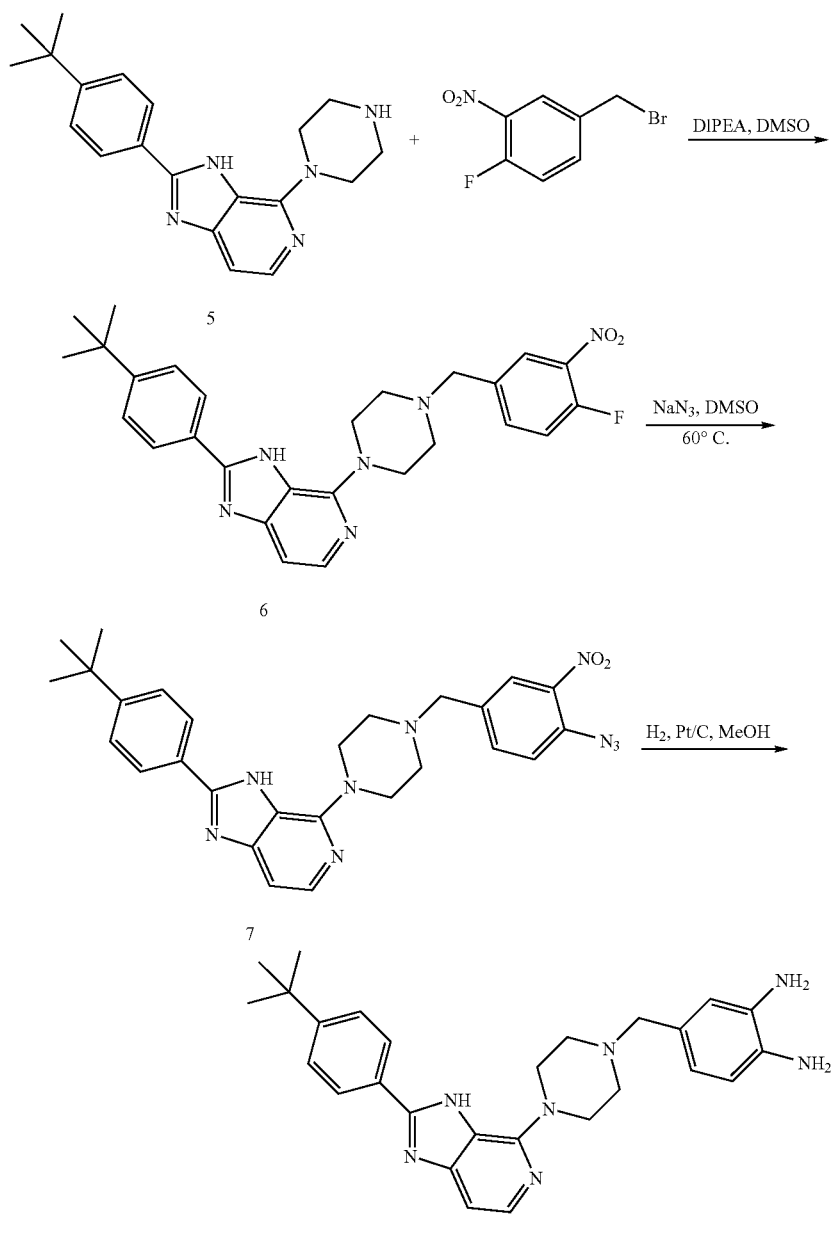

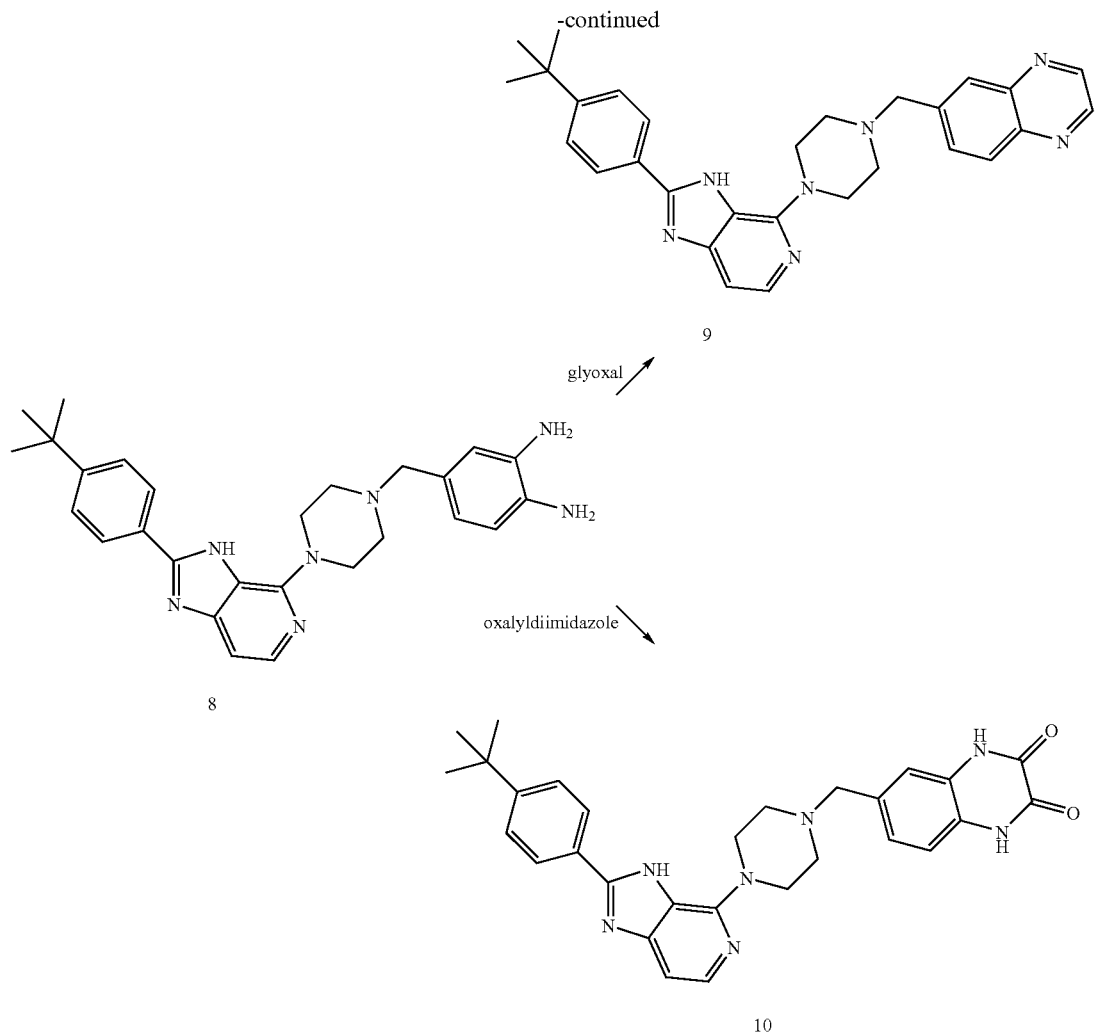

One of skill in the art will recognize that Schemes 3-4 can be adapted to produce the other compounds and pharmaceutically acceptable salts of compounds according to the present invention.

Therapeutic Administration

When administered to an animal, the compounds or pharmaceutically acceptable salts of the compounds can be administered neat or as a component of a composition that comprises a physiologically acceptable carrier or vehicle. A composition of the invention can be prepared using a method comprising admixing the compound or a pharmaceutically acceptable salt of the compound and a physiologically acceptable carrier, excipient, or diluent. Admixing can be accomplished using methods well known for admixing a compound or a pharmaceutically acceptable salt of the compound and a physiologically acceptable carrier, exipient, or diluent.

The present compositions, comprising compounds or pharmaceutically acceptable salts of the compounds of the invention can be administered orally. The compounds or pharmaceutically acceptable salts of compounds of the invention can also be administered by any other convenient route, for example, by infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the compound or a pharmaceutically acceptable salt of the compound into the bloodstream. The mode of administration is left to the discretion of the practitioner.

In one embodiment, the compound or a pharmaceutically acceptable salt of the compound is administered orally.

In another embodiment, the compound or a pharmaceutically acceptable salt of the compound is administered intravenously.

In another embodiment, it may be desirable to administer the compound or a pharmaceutically acceptable salt of the compound locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce the compound or a pharmaceutically acceptable salt of the compound into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound or a pharmaceutically acceptable salt of the compound can be formulated as a suppository, with traditional binders and excipients such as triglycerides.

In another embodiment, the compound or a pharmaceutically acceptable salt of the compound can be delivered in a vesicle, in particular a liposome (see Langer, *Science* 249: 1527-1533 (1990) and Treat et al., *Liposomes in the Therapy of Infectious Disease and Cancer* 317-327 and 353-365 (1989)).

In yet another embodiment, the compound or a pharmaceutically acceptable salt of the compound can be delivered in a controlled-release system or sustained-release system (see, e.g., Goodson, in *Medical Applications of Controlled Release*, vol. 2, pp. 115-138 (1984)). Other controlled or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment, a controlled- or sustained-release system can be placed in proximity of a target of the compound or a pharmaceutically acceptable salt of the compound, e.g., the reproductive organs, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to an animal. The physiologically acceptable excipient should be stable under the conditions of manufacture and storage and should be preserved against the contaminating action of microorganisms. Water is a particularly useful excipient when the compound or a pharmaceutically acceptable salt of the compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Liquid carriers may be used in preparing solutions, suspensions, emulsions, syrups, and elixirs. The compound or pharmaceutically acceptable salt of the compound of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and prenteral administration include water (particular containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable physiologically acceptable excipients are described in *Remington's Pharmaceutical Sciences* 1447-1676 (Alfonso R. Gennaro, ed., 19th ed. 1995).

In one embodiment, the compound or a pharmaceutically acceptable salt of the compound is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided compound or pharmaceutically acceptable salt of the compound. In tablets, the compound or pharmaceutically acceptable salt of the compound is mixed with a carrier having the necessary compression properties in suitable proportions and compacted in the shape and size desired. The powders and tablets can contain up to about 99% of the compound or pharmaceutically acceptable salt of the compound.

Capsules may contain mixtures of the compounds or pharmaceutically acceptable salts of the compounds with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrroldine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, the compositions can be coated to delay disintegration and absorption in the gastrointestinal tract, thereby providing a sustained action over an extended period of time. Selectively permeable membranes surrounding an osmotically active driving compound or a pharmaceutically acceptable salt of the compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment, the compound or a pharmaceutically acceptable salt of the compound can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the compound or a pharmaceutically acceptable salt of the compound is to be administered by infusion, it can be dispensed, for example, with an infusion bottle containing sterile pharmaceutical grade water or saline. Where the compound or a pharmaceutically acceptable salt of the compound is administered by injection, an ampule of sterile water for injection or saline can be provided so that the ingredients can be mixed prior to administration.

In another embodiment, the compound or pharmaceutically acceptable salt of the compound can be administered transdermally thorough the use of a transdermal patch. Transdermal administrations include administrations across the surface of the body and the inner linings of the bodily passages including epithelial and mucosal tissues. Such administrations can be carried out using the present compounds or pharmaceutically acceptable salts of the compounds, in lotions, creams, foams, patches, suspensions, solutions, and suppositories (e.g., rectal or vaginal).

Transdermal administration can be accomplished through the use of a transdermal patch containing the compound or pharmaceutically acceptable salt of the compound and a carrier that is inert to the compound or pharmaceutically acceptable salt of the compound, is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the compound or pharmaceutically acceptable salt of the compund into the blood stream, such as a semi-permeable membrane covering a reservoir containing the compound or pharmaceutically acceptable salt of the compound with or without a carrier, or a matrix containing the active ingredient.

The compounds or pharmaceutically acceptable salts of the compounds of the invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

The compound or a pharmaceutically acceptable salt of the compound can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of the compound or a pharmaceutically acceptable salt of the compound to treat or prevent a GnRH-related disorder in a minimal amount of time. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the compound or a pharmaceutically acceptable salt of the compound, and can thus reduce the occurrence of adverse side effects.

Controlled- or sustained-release compositions can initially release an amount of the compound or a pharmaceutically acceptable salt of the compound that promptly produces the desired therapeutic or prophylactic effect, and gradually and continually release other amounts of the compound or a pharmaceutically acceptable salt of the compound to maintain this level of therapeutic or prophylactic effect over an extended period of time. To maintain a constant level of the compound or a pharmaceutically acceptable salt of the compound in the body, the compound or a pharmaceutically acceptable salt of the compound can be released from the dosage form at a rate that will replace the amount of the compound or a pharmaceutically acceptable salt of the compound being metabolized and excreted from the body. Controlled-, or sustained-release of an active ingredient can be stimulated by various conditions, including but not limited to, changes in pH, changes in temperature, concentration or availability of enzymes, concentration or availability of water, or other physiological conditions or compounds.

In certain embodiments, the present invention is directed to prodrugs of the compounds or pharmaceutically acceptable salts of compounds of the present invention. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); "*Design and Application of Prodrugs*", *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Deilvery Systems*, American Chemical Society (1975).

The amount of the compound or a pharmaceutically acceptable salt of the compound that is effective for treating or preventing a GnRH-related disorder. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound or a pharmaceutically acceptable salt of the compound is administered, the effective dosage amounts correspond to the total amount administered.

The amount of the compound or a pharmaceutically acceptable salt of the compound that is effective for treating or preventing a GnRH-related disorder will typically range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 1 mg/kg to about 20 mg/kg of body weight per day.

In one embodiment, the pharmaceutical composition is in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may be given in a single dose or in two or more divided doses.

The compound or a pharmaceutically acceptable salt of the compound can be assayed in vitro or in vivo for the desired therapeutic or prophylactic activity prior to use in humans. Animal model systems can be used to demonstrate safety and efficacy.

The present methods for treating or preventing a GnRH-related disorder, can further comprise administering another therapeutic agent to the animal being administered the compound or a pharmaceutically acceptable salt of the compound. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. The compound or a pharmaceutically acceptable salt of the compound and the other therapeutic agent can act additively or, in one embodiment, synergistically. In one embodiment of the invention, where another therapeutic agent is administered to an animal, the effective amount of the compound or a pharmaceutically acceptable salt of the compound is less than its effective amount would be where the other therapeutic agent is not administered. In this case, without being bound by theory, it is believed that the compound or a pharmaceutically acceptable salt of the compound and the other therapeutic agent act synergistically.

In one embodiment, the other therapeutic agent is selected from the group consisting of at least one of androgens, estrogens, progesterones, antiestrogens, antiprogestogens, testosterone, angiotensin-converting enzyme inhibitor (such as ENALPRIL or CAPTOPRL), angiotensin II-receptor antagonist (such as LOSARTAN), renin inhibitor, bisphosphonates (bisphosphonic acids), growth hormone secretagogues (such as MK-0677), 5a-reductase 2 inhibitor (such as finasteride or episteride) a 5a-reductase 1 inhibitor (such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane), dual inhibitors of 5a-reductase 1 and 5a-reductase 2 (such as 3-oxo-4-aza-17b-(2,5-trifluoromethylphenyl-carbamoyl)-5a-androstan), antiandrogens (such as flutamide, casodex and cyproterone acetate), alpha-1 blockers (such as prazosin, terazosin, doxazosin, tamsulosin, and alfuzosin), growth hormone, and luteinizing hormone releasing compounds (such as a peptide, including leuprorelin, gonadorelin, buserelin, triptorelin, goserelin, nafarelin, histrelin, deslorelin, meterlin and recirelin, or a natural hormone or analog thereof).

For example, when used with compounds or pharmaceutically acceptable salts of compounds of the present invention: androgens, estrogens, progesterones, antiestrogens and antiprogestogens find use in the treatment of endometriosis, fibroids, and in contraception; testosterone or other androgens or antiprogestogens find use in men as a contraceptive; angiotensin-converting enzyme inhibitors, angiotensin II-receptor antagonists, and renin inhibitor find use in the treatment of uterine fibroids; bisphosphonates (bisphosphonic acids) and growth hormone secretagogues find use in the treatment and prevention of disturbances of calcium, phosphate and bone metabolism, in particular, for the prevention of bone loss during therapy with the GnRH antagonist, and in combination with estrogens, progesterones, antiestrogens, antiprogesterones and/or androgens for the prevention or treatment of bones loss or hypogonadal symptoms such as hot flashes during therapy with the GnRH antagonist; and growth hormone, growth hormone releasing hormone or growth hormone secretagogues, to delay puberty in growth hormone deficient children. Additional therapeutic agents useful in combination with the compounds or pharmaceutically acceptable salts of compounds of the present invention include 5a-reductase 2 inhibitor, 5a-reductase 1 inhibitor, dual inhibitors of 5a-reductase 1 and 5a-reductase 2, antiandrogens, alpha-1 blockers, and compounds having luteinizing hormone releasing activity.

In one embodiment, the compound or a pharmaceutically acceptable salt of the compound is administered concurrently with another therapeutic agent.

In one embodiment, a composition comprising an effective amount of the compound or a pharmaceutically acceptable salt of the compound and an effective amount of another therapeutic agent within the same composition can be administered.

In another embodiment, a composition comprising an effective amount of the compound or a pharmaceutically acceptable salt of the compound and a separate composition comprising an effective amount of another therapeutic agent can be concurrently administered. In another embodiment, an effective amount of the compound or a pharmaceutically acceptable salt of the compound is administered prior to or subsequent to administration of an effective amount of another therapeutic agent. In this embodiment, the compound or a pharmaceutically acceptable salt of the compound is administered while the other therapeutic agent exerts its therapeutic effect, or the other therapeutic agent is administered while the compound or a pharmaceutically acceptable salt of the compound exerts its preventative or therapeutic effect for treating or preventing a GnRH-related disorder.

Thus, in one embodiment, the invention provides a composition comprising an effective amount of the compound or a pharmaceutically acceptable salt of the compound of the present invention and a pharmaceutically acceptable carrier.

In another embodiment, the composition further comprises a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

In another embodiment, the pharmaceutically acceptable carrier is suitable for oral administration and the composition comprises an oral dosage form.

Therapeutic or Prophylactic Uses

In one embodiment, the compounds or pharmaceutically acceptable salts of the compounds of the present invention are useful as GnRH receptor antagonists. Accordingly, the compounds and pharmaceutically acceptable salts of the compounds of the present invention are useful for treating a mammal with a GnRH-related disorder.

In one embodiment, the invention provides a method for treating a GnRH-related disorder, comprising administering to a mammal in need thereof a compound or a pharmaceutically acceptable salt of the compound of Formula (I) or Formula (Ia) in an amount effective to treat a GnRH-related disorder.

In one embodiment, the GnRH-related disorder is a sex hormone-related condition.

In one embodiment, the GnRH-related disorder is a sex hormone-dependent cancer. In another embodiment, the GnRH-related disorder is prostate cancer, testicular cancer, uterine cancer, ovarian cancer, breast cancer, or pituitary gonadotrophe adenomas. In one embodiment, the GnRH-related disorder is breast cancer.

In another embodiment, the GnRH-related disorder is endometriosis, polycystic ovarian disease, uterine fibroids, primary hirsutism, luteinizing hormone surge, or precocious puberty.

In another embodiment, the invention provides a method for preventing pregnancy, comprising administering to a female mammal the compound or pharmaceutically acceptable salt of the compound of Formula (I) or Formula (Ia) in an amount effective to prevent pregnancy.

In yet another embodiment, the methods of the present invention further comprise administering to the mammal a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

In one embodiment, the present invention is directed to a method for modulating the activity of a Gonadotropin Releasing Hormone receptor, comprising contacting the receptor with an effective amount of a compound or pharmaceutically acceptable salt of the compound of Formula (I) or Formula (Ia). In one embodiment, the method further comprises determining the activity of the receptor. In one embodiment, the step of determining the activity of the receptor is performed before the step of contacting the receptor with the compound or a pharmaceutically acceptable salt of the compound. In another embodiment, the step of determining the activity of the receptor is performed after the step of contacting the receptor with the compound or a pharmaceutically acceptable salt of the compound.

The compounds and pharmaceutically acceptable salts of the compounds of Formula (I) or Formula (Ia) are also useful in the manufature of medicaments for treating a GnRH-related disorder in a mammal.

Accordingly, in one embodiment, the invention provides the use of a compound or pharmaceutically acceptable salt of the compound of Formula (I) or Formula (Ia) for the manufacture of a medicament for treating a GnRH-related disorder.

In one embodiment, the GnRH-related disorder is a sex hormone-related condition.

In one embodiment, the GnRH-related disorder is a sex hormone-dependent cancer. In another embodiment, the GnRH-related disorder is prostate cancer, testicular cancer, uterine cancer, ovarian cancer, breast cancer, or pituitary gonadotrophe adenomas. In one embodiment, the GnRH-related disorder is breast cancer.

In another embodiment, the GnRH-related disorder is endometriosis, polycystic ovarian disease, uterine fibroids, primary hirsutism, luteinizing hormone surge, or precocious puberty.

In another embodiment, the invention provides the use of a compound or pharmaceutically acceptable salt of the compound of Formula (I) or Formula (Ia) in the manufacture of a medicament for preventing pregnancy in a female mammal.

In yet another embodiment, the uses of the compounds or pharmaceutically acceptable salts of compounds of the present invention further comprise the use of a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof in the manufacture of the medicaments of the present invention.

In one embodiment, the present invention is directed to the use of a compound or pharmaceutically acceptable salt of the compound of Formula (I) or Formula (Ia) for the manufacture of a medicament for modulating the activity of a Gonadotropin Releasing Hormone receptor. In one embodiment, the medicament is also for determining the activity of the receptor.

EXAMPLES

General Methods:
The following HPLC and LC/MS methods were used for the syntheses outlined in the Examples.

Method A: Column: Xterra MS C18, 5µ, 50×2.1 mm. Mobile phase: 90/10-5/95 water (0.1% formic acid)/acetonitrile (0.1% formic acid), 2 minutes, hold 1.5 minutes. Flow rate: 0.8 mL/min. Detection: 210-400 nm.

Method D: Column: Xterra reverse phase 18, 3.5µ, 150×4.6 mm. Mobile phase: 85/15 to 5/95 phosphate buffer (pH=2.1)/acetonitrile and methanol (1:1) for 10 minutes, hold 4 minutes, 1.2 mL/minute. Detection: 210-370 nm.

Method E: YMC CombiPrep ProC18 50×20 mm I.D. column, S-5 µm, 12 nm. Flow rate 20 mL/minute. Gradient: 10/90 Acetonitrile/Water (0.1% TFA in both solvents) to 100% acetonitrile over 10 minutes then hold for three minutes at 100% acetonitrile and ramp back to 10/90 acetonitrile/water over two minutes.

Example 1

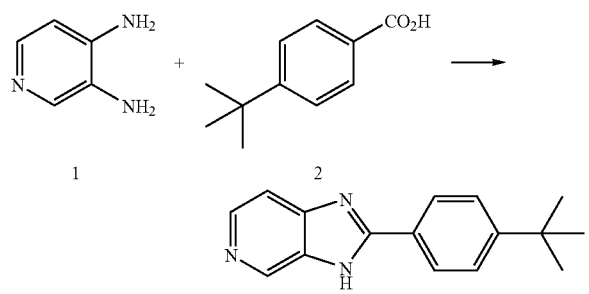

2-(4-tert-butyl-phenyl)-3H-imidazo[4,5-b]pyridine (3. To a solution of 3,4-diaminopyridine (1) (1.5 g, 14 mmol) and 4-t-butylbenzoic acid (2) (2.5 g, 14 mmol) in N-methylpyrrolidinone (20 mL) was added EDC (2.7 g, 14 mmol) and the mixture stirred for 2.5 hours at 20° C. Acetic acid (20 mL) was added to the reaction mixture and it was heated quickly to 100° C. and held at this temperature for 1 hour. After cooling to room temperature the mixture was diluted with ethyl acetate (300 mL), washed with 1M sodium carbonate solution (100 mL) and water (5×200 mL), dried over MgSO$_4$, and evaporated under reduced pressure. The residue was chromatographed on silica gel and eluted with a gradient of ethyl acetate:hexanes (3:1) to ethyl acetate (100%) to ethyl acetate:methanol (19:1). This left the desired product 3 (1.3 g, 37%), the starting acid 2 (0.33 g, 13%) and the diamine bisamide of 1 (1.0 g, 17%). LC/MS (Method A): R$_t$=0.99 minutes, [M+H]$^+$=252, purity=87%.

Example 2

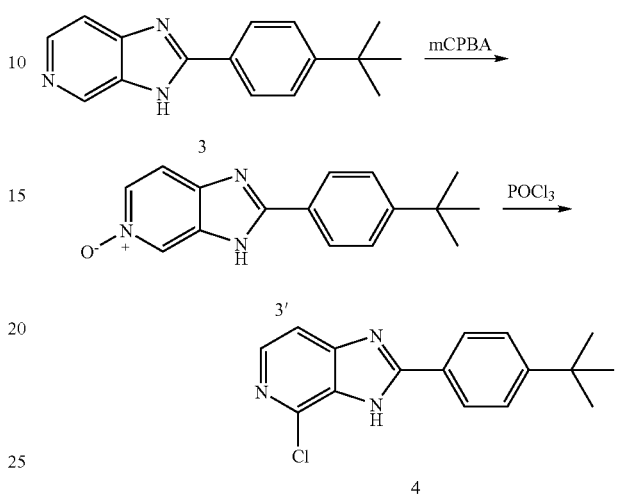

2-(4-tert-butyl-phenyl)-4-chloro-3H-imidazo[4,5-c]pyridine (4). A solution of the imidazopyridine 3 (1.2 g, 4.8 mmol) in dichloromethane (50 mL) was treated with 70% mCPBA (1.7 g, 9.6 mmol). The mixture stirred at 20° C. for 2 hours, then at reflux temperature for 3 hours. The solvent was evaporated, the residue was redissolved in ethyl acetate (100 mL), and washed with 1 M sodium carbonate (50 mL) and water (2×50 mL). The combined aqueous layers were neutralized (conc. HCl, pH=7) and the product separated out as an emulsion. The mixture was allowed to stand for 24 hours and during this time the product settled to the bottom of the flask. The supernatant was decanted, water (50 mL) was added to the product and decanted. This procedure was repeated, then the product was dried under high vacuum to obtain 3'. The residue was dissolved in phosphorous oxychloride (30 mL), stirred and heated to reflux for 3 hours. The reaction mixture was evaporated under reduced pressure, the residue was dissolved in ethyl acetate (100 mL) and saturated sodium bicarbonate solution (100 mL) and separated. The aqueous layer was extracted with ethyl acetate (50 mL) and the organic layers were combined, dried over MgSO$_4$, and evaporated to leave the product chloride 4 (1.3 g, 95%). LC/MS (method A); R$_t$=1.63 minutes, [M+H]$^+$=286 and 288, purity=92.3%.

Example 3

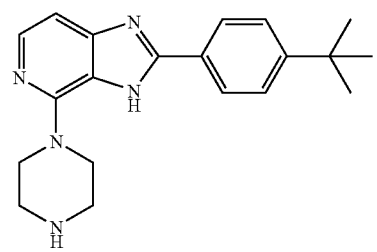

2-(4-tert-butyl-phenyl)-4-piperazin-1-yl-3H-imidazo[4,5-c]pyridine (5). A solution of the chloroimidazopyridine 4 (0.75 g, 2.6 mmol) and piperazine (6.8 g, 79 mmol) in DMSO (15 mL) was heated to 140° C. for 3 hours. During this time, the reaction mixture was gently swirled every 30 minutes to redissolve piperazine on the upper walls of the flask. After cooling to room temperature, ethyl acetate (150 mL) was added and the solution was washed with water (3×100 mL), dried over MgSO$_4$, and evaporated to leave a yellow powder (0.75 g, 86%). LC/MS (method A); R$_t$=0.90 minutes, [M+H]$^+$=336, purity>99%.

Example 4

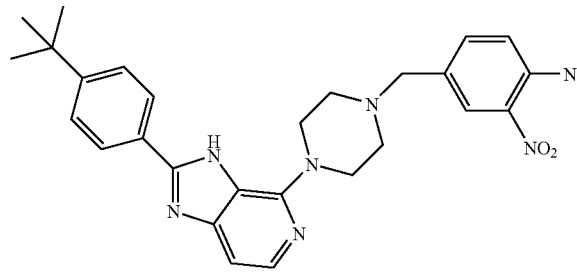

7

4-[4-(4-azido-3-nitro-benzyl)-piperazin-1-yl]-2-(4-tert-butyl-phenyl)-3H-imidazo[4,5-c]pyridine (7). A solution of the piperazine 5 (0.10 g, 0.30 mmol), 4-fluoro-3-nitrobenzyl bromide (70 mg, 0.30 mmol) and diisopropylethylamine (39 mg, 0.30 mmol, 54 μL) in DMSO (1 mL) was stirred at room temperature for 18 hours. The reaction mixture was diluted with ethyl acetate (25 mL), washed with water (3×20 mL), dried over MgSO$_4$, and evaporated. The residue was chromatographed (silica gel, ethyl acetate) to leave a light yellow foamy solid, crude 6 (0.11 g, 75%). A sample of crude 6 (0.10 g, 0.20 mmol) was dissolved in DMSO (2 mL), treated with sodium azide (65 mg, 1.0 mmol), stirred, and heated to 60° C. for 4 hours. After cooling to room temperature the reaction mixture was diluted with ethyl acetate (25 mL), washed with water (3×20 mL), dried (MgSO$_4$) and evaporated to leave the product as a beige foamy solid 7 (0.11 g, 100%). LC/MS (method A); R$_t$=1.36 minutes, [M−H]$^-$=510, purity>99%.

Example 5

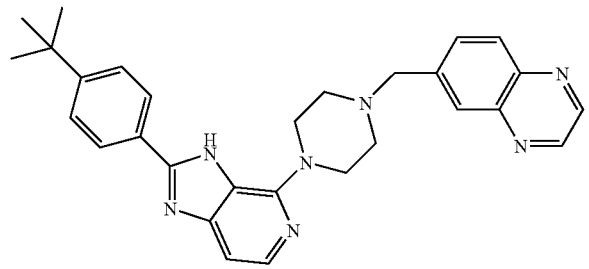

9

6-{4-[2-(4-tert-butyl-phenyl)-3H-imidazo[4,5-c]pyridine-4-yl]-piperazin-1-ylmethyl}-quinoxaline (9). A mixture of the nitroazide 7 (0.10 g, 0.20 mmol) and 10% Pt/C (25 mg) in MeOH (3 mL) was purged with hydrogen and stirred under a blanket of hydrogen at 1 atmosphere for 3 hours. The catalyst was filtered through diatomaceous earth, washed with MeOH (3×5 mL), and evaporated under reduced pressure to leave 79 mg of product (87%). A sample of the phenylenediamine 8 (37 mg, 81 μmol) was dissolved in MeOH (1 mL) and treated with 40% glyoxal (aqueous, 23 mg, 0.16 mmol, 30 μL). The reaction mixture was stirred for 18 hours, then purified by direct injection onto an HPLC (method E). The product fractions were identified by LC/MS (method A), combined and evaporated to leave the product 9 as a tan powder, bistrifluoroacetate salt (42 mg, 74%). HPLC (method D); R$_t$=6.61, purity=97.6%. LC/MS (method A); R$_t$=1.30 minutes, [M−H]$^-$=476.

Example 6

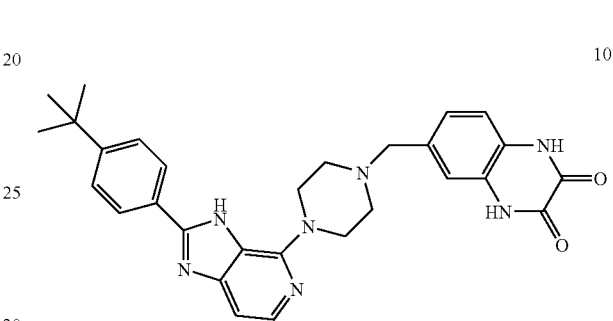

10

6-{4-[2-(4-tert-butyl-phenyl)-3H-imidazo[4,5-c]pyridine-4-yl]-piperazin-1-ylmethyl}-1,4-dihydro-quinoxaline-2,3-dione (10). A mixture of the nitroazide 7(0.10 g, 0.20 mmol) and 10% Pt/C (25 mg) in MeOH (3 mL) was purged with hydrogen and stirred under a blanket of hydrogen at 1 atmosphere for 3 hours. The catalyst was filtered through diatomaceous earth, washed with MeOH (3×5 mL) and evaporated under reduced pressure to leave 79 mg of product (87%). A sample of the phenylenediamine 8 (37 mg, 81 μmol) was dissolved in THF (1 mL), treated with oxalyldiimidazole (30 mg, 0.16 mmol) and stirred 18 hours. Water (0.2 mL) was added to the reaction mixture and it stirred an additional 1 hour. The solution was injected directly onto an HPLC (method E), the product fractions were identified by LC/MS (method A), combined and evaporated to provide the product 10 as a white powder, bistrifluoroacetate salt (19 mg, 32%). HPLC (method D); R$_t$=5.60 mins., purity=94.5%. LC/MS (method A); R$_t$=1.15 minutes, [M−H]$^-$=508, [M+H]$^+$=510.

Example 7

Biological Evaluation

COS cell membranes containing human GnRH receptors were incubated with radioactively labeled D-trp6 GnRH in the presence of increasing concentrations of test compound. Membrane bound radioactivity was measured after separating the free radioactivity by filtration method, and IC$_{50}$ values were calculated using SAS analysis system. (See, "Receptor-binding Affinity of Gonadotropin-releasing Hormone Analogs: Analysis by Radioligand-receptor assay" *Endocrinology*, 106:1154-1159 (1980)).

All compounds tested had hGnRH binding IC$_{50}$'s of less than 10 micromolar.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound of the formula (I):

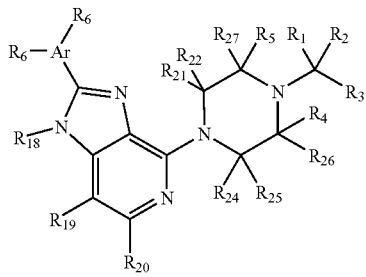

(I)

or a pharmaceutically acceptable salt thereof,
wherein
Ar is phenyl, 2-thiophenyl or 3-thiophenyl;
$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;
$R_3$ is one of the following:

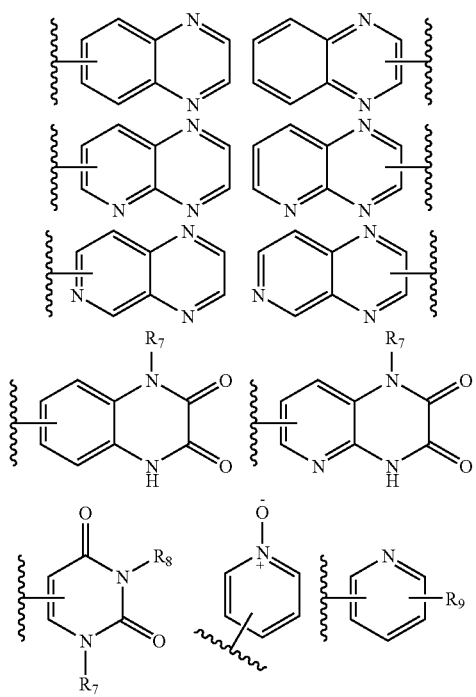

-continued

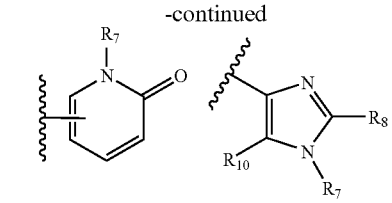

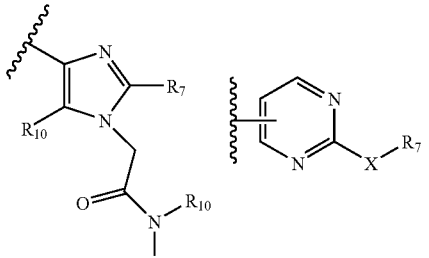

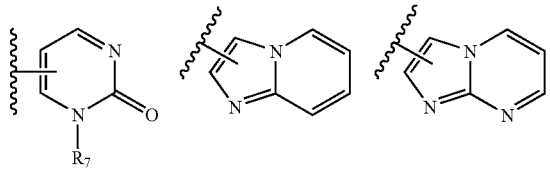

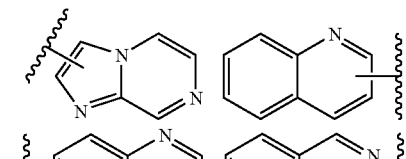

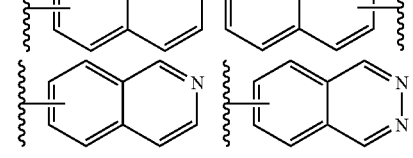

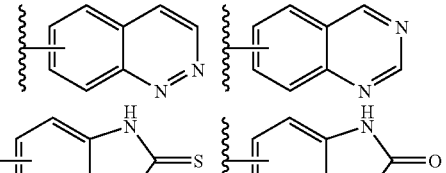

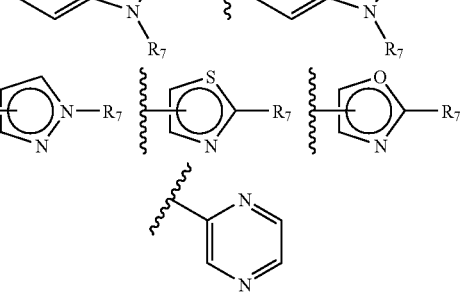

each $R_3$ also having up to three $R_{10}$ substituents attached to a ring of $R_3$ containing at least one N;

$R_4$, $R_5$, $R_{10}$, $R_{18}$, $R_{19}$, $R_{20}$, $R_{21}$, $R_{22}$, $R_{23}$, $R_{24}$, $R_{25}$, $R_{26}$, and $R_{27}$ are each independently hydrogen; or linear or branched $(C_1-C_6)$-alkyl, $(C_2-C_6)$-alkenyl, or $(C_2-C_6)$-alkynyl;

each $R_6$ is independently hydrogen; linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; —NR$_{13}$R$_{14}$; —C(OH)(CF$_3$)$_2$; —CH(CF$_3$)$_2$; C(CF$_3$)$_3$; —XR$_{13}$; or —COR$_{13}$; and when two R$_6$ are ortho to each other, they may together form a five- to seven-membered cyclic group containing up to 3 heteroatoms selected from N, O, or S, and wherein the cyclic group formed by the ortho R$_6$ groups is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2$)$_n$OR$_{23}$;

R$_7$ and R$_9$ are each independently hydrogen; linear or branched (C$_1$-C$_6$)-alkyl, (C$_2$-C$_6$)-alkenyl, or (C$_2$-C$_6$)-alkynyl; —R$_{11}$XR$_{12}$; —(CH$_2$)$_n$R$_{17}$; —COXR$_{11}$; —XR$_{11}$; —CO$_2$R$_{11}$; or —CONR$_{11}$R$_{12}$;

R$_8$ is hydrogen; linear or branched (C$_1$-C$_6$)-alkyl, (C$_2$-C$_6$)-alkenyl, or (C$_2$-C$_6$)-alkynyl; —(CH$_2$)$_m$CO$_2$R$_{11}$; or —(CH$_2$)$_m$CONR$_{11}$R$_{12}$;

R$_{11}$ and R$_{12}$ are each independently hydrogen; linear or branched (C$_1$-C$_6$)-alkyl, (C$_2$-C$_6$)-alkenyl, or (C$_2$-C$_6$)-alkynyl; or R$_{11}$ and R$_{12}$ may together form a three- to seven-membered heterocyclic group containing up to 3 heteroatoms selected from N, O, or S;

R$_{13}$ and R$_{14}$ are each independently hydrogen; linear or branched (C$_1$-C$_6$)-alkyl, (C$_2$-C$_6$)-alkenyl, or (C$_2$-C$_6$) alkynyl, each optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, or —CON(R$_{23}$)$_2$; aryl; or aryl optionally substituted with one to three substituents selected from halogen, R$_{15}$, —OR$_{15}$, or —NR$_{15}$R$_{16}$; or R$_{13}$ and R$_{14}$ may together form a three- to seven-membered heterocyclic group containing up to 3 heteroatoms selected from N, O, or S, and wherein the heterocyclic group formed by R$_{13}$ and R$_{14}$ is optionally substituted with halogen, —N$_3$, —NO$_2$, —CN, —OR$_{23}$, —SR$_{23}$, —SO$_2$R$_{23}$, —SO$_2$N(R$_{23}$)$_2$, —N(R$_{23}$)$_2$, —COR$_{23}$, —CO$_2$R$_{23}$, —NR$_{23}$CO$_2$R$_{23}$, —NR$_{23}$COR$_{23}$, —NR$_{23}$CON(R$_{23}$)$_2$, —CON(R$_{23}$)$_2$, or —CH$_2$)$_n$OR$_{23}$;

R$_{15}$ and R$_{16}$ are each independently hydrogen; or linear or branched (C$_1$-C$_6$)-alkyl, (C$_2$-C$_6$)-alkenyl, or (C$_2$-C$_6$)-alkynyl; or both R$_{15}$ and R$_{16}$ may together form a three- to seven-membered heterocyclic group containing up to 3 heteroatoms selected from N, O, or S;

R$_{17}$ is phenyl, 2-pyridyl, 3-pyridyl, or 4-pyridyl;

X is —O—, —NR$_{12}$—, or —SO$_m$—;

each m is independently 0, 1, or 2; and each n is independently 0, 1, 2, 3, or 4.

2. The compound or pharmaceutically acceptable salt of the compound of claim 1, wherein Ar is phenyl.

3. The compound or pharmaceutically acceptable salt of the compound of claim 2, wherein one R$_6$ substituent is attached at the 4 position of phenyl.

4. The compound or pharmaceutically acceptable salt of the compound of claim 1, wherein R$_1$ is methyl and R$_2$ is hydrogen.

5. The compound or pharmaceutically acceptable salt of the compound of claim 1, wherein R$_4$ is methyl or ethyl and R$_5$ is hydrogen.

6. The compound or pharmaceutically acceptable salt of the compound of claim 1, wherein when R$_4$ is other than hydrogen, the compound or pharmaceutically acceptable salt of the compound is the S-enantiomer with respect to the carbon to which $_4$ is bound.

7. The compound or pharmaceutically acceptable salt of the compound of claim 1, wherein R$_6$ is independently hydrogen, ethyl, t-butyl, —N(CH$_2$CH$_3$)$_2$, pyrrolidine, 2-hydroxymethylpyrrolidine, or isopropyl.

8. The compound or pharmaceutically acceptable salt of the compound of claim 1, wherein R$_3$ is

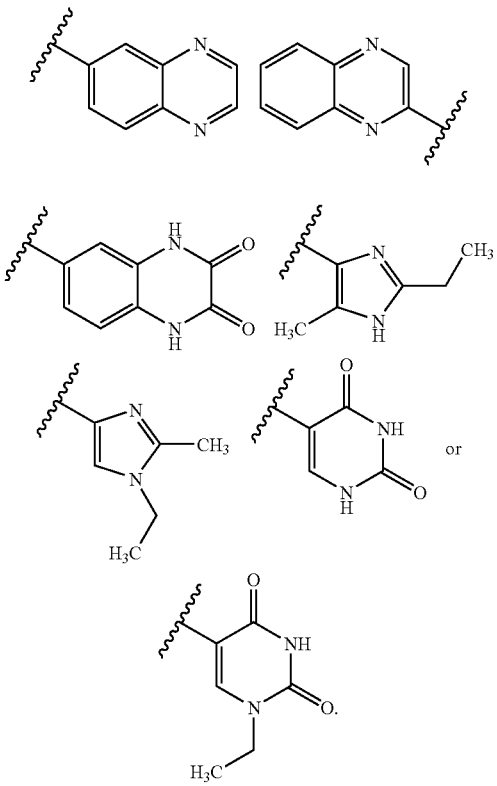

9. The compound or pharmaceutically acceptable salt of the compound of claim 1, wherein R$_3$ is

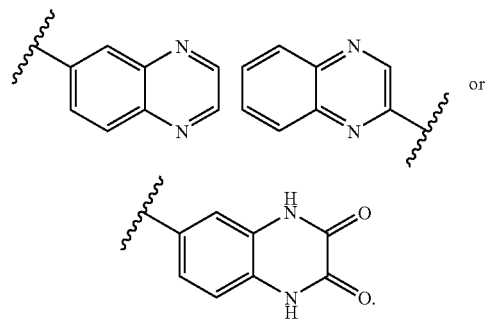

10. The compound or pharmaceutically acceptable salt of the compound of claim 1, wherein R$_2$, R$_5$, R$_{18}$, R$_{19}$, R$_{20}$, R$_{21}$, R$_{22}$, R$_{24}$, R$_{25}$, R$_{26}$, and R$_{27}$ are each hydrogen;

R$_1$ and R$_4$ are each independently hydrogen, methyl, or ethyl;

Ar is phenyl;

one R$_6$ is attached at the 4-position of phenyl;

each R$_6$ is ethyl, t-butyl, —N(CH$_2$CH$_3$)$_2$, pyrrolidine, 2-hydroxymethylpyrrolidine, or isopropyl; and R₃ is

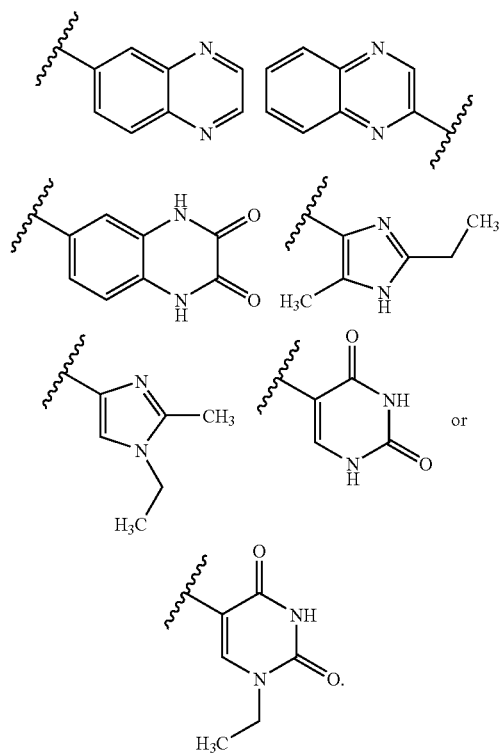

11. The compound or pharmaceutically acceptable salt of the compound of claim 1, wherein the compound is
- 6-{4-[2-(4-tert-butyl-phenyl)-1H-imidazo[4,5-c]pyridin-4-yl]-piperazin-1-ylmethyl}quinoxaline;
- 6-{4-[2-(4-tert-butyl-phenyl)-1H-imidazo[4,5-c]pyridin-4-yl]-piperazin-1-ylmethyl}-1,4-dihydroquinoxaline-2,3-dione;
- 2-{4-[2-(4-tert-butyl-phenyl)-1H-imidazo[4,5-c]pyridin-4-yl]-piperazin-1-ylmethyl}-quinoxaline;
- 2-(4-tert-butyl-phenyl)-4-[4-(2-ethyl-5-methyl-1H-imidazol-4-ylmethyl)-piperazin-1-yl]-1H-imidazo[4,5-c]pyridine;
- 2-(4-tert-butyl-phenyl)-4-[4-(1,2-dimethyl-1H-imidazol-4-ylmethyl)-piperazin-1-yl]-1H-imidazo[4,5-c]pyridine;
- 5-{4-[2-(4-tert-butyl-phenyl)-1H-imidazo[4,5-c]pyridin-4-yl]-piperazin-1-ylmethyl}-1H-pyrimidine-2,4-dione; or
- 5-{4-[2-(4-tert-butyl-phenyl)-1H-imidazo[4,5-c]pyridin-4-yl]-piperazin-1-ylmethyl}-1-ethyl-1H-pyrimidine-2,4-dione.

12. A compound of the formula (Ia):

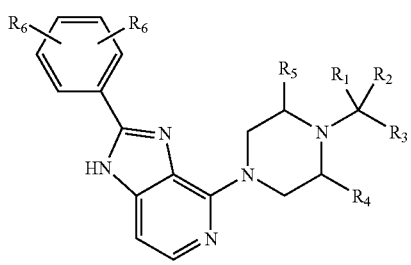

(Ia)

or a pharmaceutically acceptable salt thereof, wherein
$R_1$ and $R_2$ are each independently hydrogen; or linear or branched $(C_1-C_6)$-alkyl, $(C_2-C_6)$-alkenyl, or $(C_2-C_6)$-alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-(CH_2)_nOR_{23}$;

$R_3$ is one of the following:

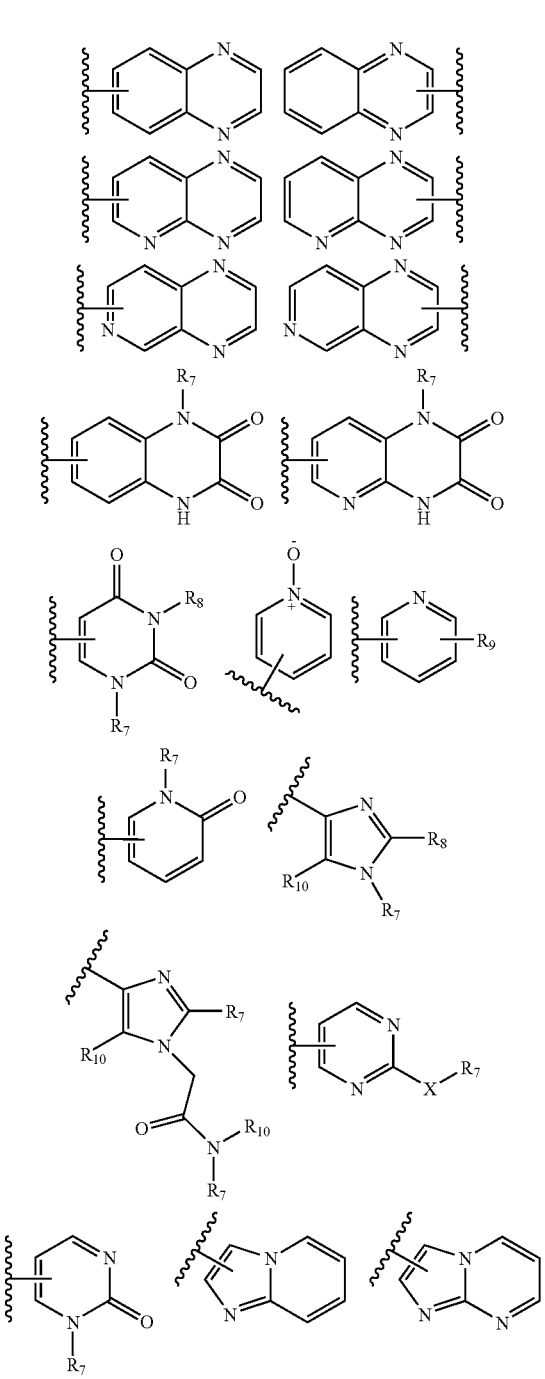

-continued

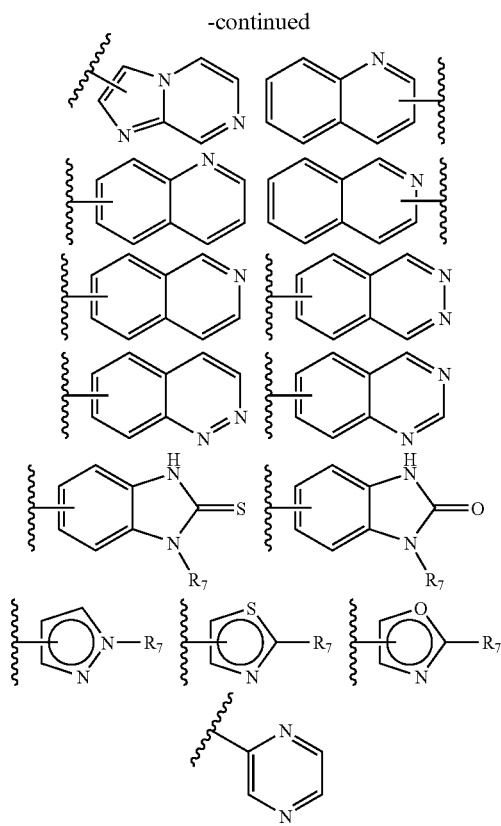

each $R_3$ also having up to three $R_{10}$ substituents attached to a ring of $R_3$ containing at least one N;

$R_4$, $R_5$, $R_{10}$, and $R_{23}$ are each independently hydrogen; or linear or branched $(C_1-C_6)$-alkyl, $(C_2-C_6)$-alkenyl, or $(C_2-C_6)$-alkynyl;

each $R_6$ is independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —$C(OH)(CF_3)_2$; —$CH(CF_3)_2$; —$C(CF_3)_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched $(C_1-C_6)$-alkyl, $(C_2-C_6)$-alkenyl, or $(C_2-C_6)$-alkynyl; $R_{11}XR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched $(C_1-C_6)$-alkyl, $(C_2-C_6)$-alkenyl, or $(C_2-C_6)$-alkynyl; —$(CH_2)_mCO_2R_{11}$; or —$(CH_2)_mCONR_{11}R_{12}$;

$R_{11}$ and $R_{12}$ are each independently hydrogen; linear or branched $(C_1-C_6)$-alkyl, $(C_2-C_6)$-alkenyl, or $(C_2-C_6)$-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched $(C_1-C_6)$-alkyl, $(C_2-C_6)$-alkenyl, or $(C_2-C_6)$-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; aryl; or aryl optionally substituted with one to three substituents selected from halogen, $R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched $(C_1-C_6)$-alkyl, $(C_2-C_6)$-alkenyl, or $(C_2-C_6)$-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

X is —O—, —$NR_{12}$—, or —$SO_m$—;

each m is independently 0, 1, or 2; and each n is independently 0, 1, 2, 3, or 4.

13. The compound or pharmaceutically acceptable salt of the compound of claim 12, wherein $R_1$ and $R_4$ are each independently hydrogen, methyl, or ethyl;

$R_2$ and $R_5$ are hydrogen;

one $R_6$ is attached at the 4-position of phenyl;

each $R_6$ is ethyl, t-butyl, —$N(CH_2CH_3)_2$, pyrrolidine, 2-hydroxymethylpyrrolidine, or isopropyl; and $R_3$ is

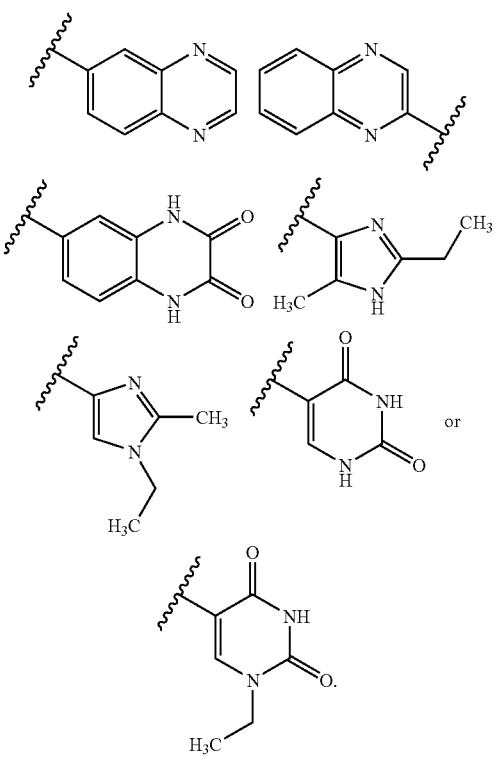

14. A composition comprising an effective amount of the compound or a pharmaceutically acceptable salt of the compound of claim 1 and a pharmaceutically acceptable carrier.

15. The composition of claim 14, further comprising a therapeutic agent selected from the group consisting of androgen, estrogen, progesterone, antiestrogen, antiprogestogen, testosterone, angiotensin-converting enzyme inhibitor, angiotensin II-receptor antagonist, renin inhibitor, bisphosphonate, growth hormone secretagogue, 5a-reductase 2 inhibitor, a 5a-reductase 1 inhibitor, a dual inhibitor of 5a-reductase 1 and 5a-reductase 2, antiandrogen, alpha-1 blockers, growth hormone, and luteinizing hormone releasing compound; or a combination thereof.

16. The composition of claim 14, wherein the pharmaceutically acceptable carrier is suitable for oral administration and the composition comprises an oral dosage form.

17. A compound of the formula (I):

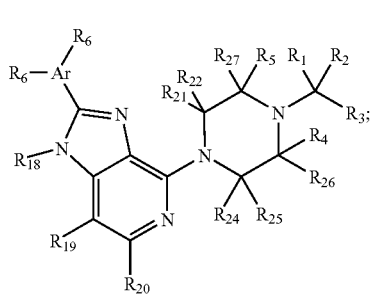

(I)

prepared by the method comprising:

a) reacting a compound of the formula (II):

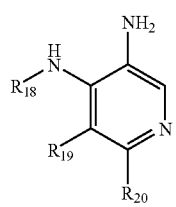

(II)

with an aryl acid under conditions effective to bring about cyclization, thereby providing an imidazo[4,5-c]pyridine having the formula (III):

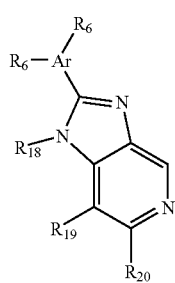

(III)

b) treating the imidazo[4,5-c]pyridine (III) under conditions effective to bring about chlorination, thereby providing a 4-chloro-imidazo[4,5-c]pyridine having the Formula (IV):

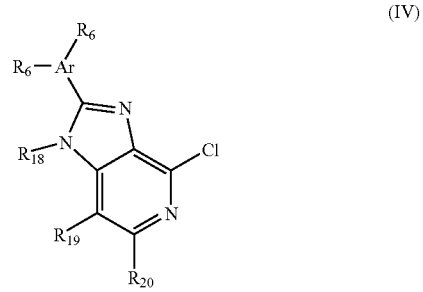

(IV)

c) reacting the 4-chloro-imidazo[4,5-c]pyridine (IV) with a piperazine under conditions effective to produce a 4-piperazine-imidazo[4,5-c]pyridine having the formula (V):

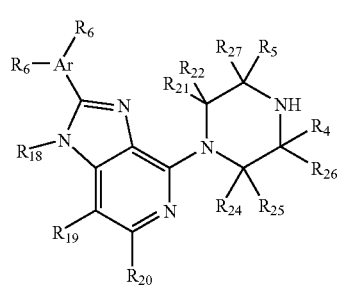

(V)

and d) reacting the free amine of the 4-piperazine-imidazo[4,5-c]pyridine of the formula (V) under conditions effective to provide the compound of formula (I);

wherein Ar is phenyl, 2-thiophenyl or 3-thiophenyl;

$R_1$ and $R_2$ are each independently hydrogen; or linear or branched $(C_1-C_6)$-alkyl, $(C_2-C_6)$-alkenyl, or $(C_2-C_6)$ alkynyl, each optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, or $-CON(R_{23})_2$; or $R_1$ and $R_2$ may together form a three- to seven-membered cycloalkyl group, wherein the cycloalkyl group formed by $R_1$ and $R_2$ is optionally substituted with halogen, $-N_3$, $-NO_2$, $-CN$, $-OR_{23}$, $-SR_{23}$, $-SO_2R_{23}$, $-SO_2N(R_{23})_2$, $-N(R_{23})_2$, $-COR_{23}$, $-CO_2R_{23}$, $-NR_{23}CO_2R_{23}$, $-NR_{23}COR_{23}$, $-NR_{23}CON(R_{23})_2$, $-CON(R_{23})_2$, or $-CH_2)_nOR_{23}$;

$R_3$ is one of the following:

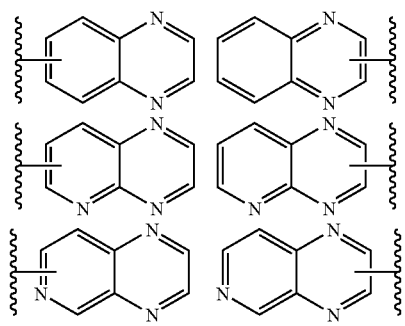

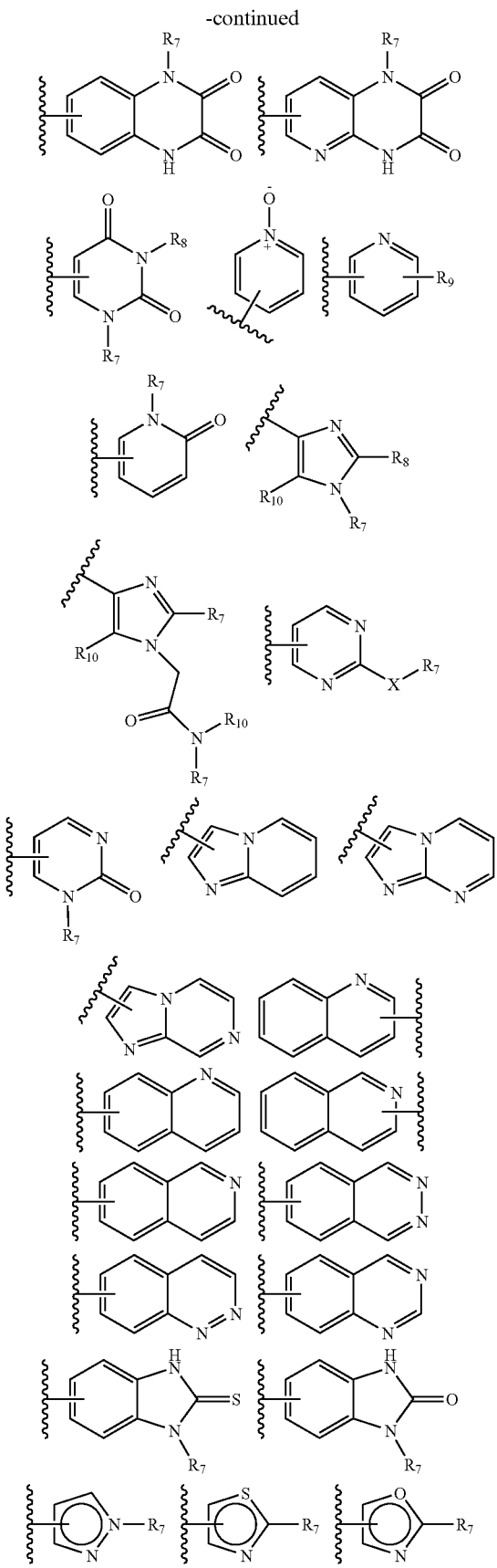

each $R_3$ also having up to three $R_{10}$ substituents attached to a ring of $R_3$ containing at least one N;

$R_4$, $R_5$, $R_{10}$, $R_{18}$, $R_{19}$, $R_{20}$, $R_{21}$, $R_{22}$, $R_{23}$, $R_{24}$, $R_{25}$, $R_{26}$, and $R_{27}$ are each independently hydrogen; or linear or branched ($C_1$-$C_6$)-alkyl, ($C_2$-$C_6$)-alkenyl, or ($C_2$-$C_6$)-alkynyl;

each $R_6$ is independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or —$CON(R_{23})_2$; —$NR_{13}R_{14}$; —C(OH)(CF$_3$)$_2$; —CH(CF$_3$)$_2$; —C(CF$_3$)$_3$; —$XR_{13}$; or —$COR_{13}$; and when two $R_6$ are ortho to each other, they may together form a five- to seven-membered cyclic group containing up to 3 heteroatoms selected from N, O, or S, and wherein the cyclic group formed by the ortho $R_6$ groups is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_7$ and $R_9$ are each independently hydrogen; linear or branched ($C_1$-$C_6$)-alkyl, ($C_2$-$C_6$)-alkenyl, or ($C_2$-$C_6$)-alkynyl; —$R_{11}XR_{12}$; —$(CH_2)_nR_{17}$; —$COXR_{11}$; —$XR_{11}$; —$CO_2R_{11}$; or —$CONR_{11}R_{12}$;

$R_8$ is hydrogen; linear or branched ($C_1$-$C_6$)-alkyl, ($C_2$-$C_6$)-alkenyl, or ($C_2$-$C_6$)-alkynyl; —$(CH_2)_mCO_2R_{11}$; or —$(CH_2)_mCONR_{11}R_{12}$;

$R_{11}$ and $R_{12}$ are each independently hydrogen; linear or branched ($C_1$-$C_6$)-alkyl, ($C_2$-$C_6$)-alkenyl, or ($C_2$-$C_6$)-alkynyl; or $R_{11}$ and $R_{12}$ may together form a three- to seven-membered heterocyclic group containing up to 3 heteroatoms selected from N, O, or S;

$R_{13}$ and $R_{14}$ are each independently hydrogen; linear or branched ($C_1$-$C_6$)-alkyl, ($C_2$-$C_6$)-alkenyl, or ($C_2$-$C_6$)-alkynyl, each optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, or $CON(R_{23})_2$; aryl; or aryl optionally substituted with one to three substituents selected from halogen, —$R_{15}$, —$OR_{15}$, or —$NR_{15}R_{16}$; or $R_{13}$ and $R_{14}$ may together form a three- to seven-membered heterocyclic group containing up to 3 heteroatoms selected from N, O, or S, and wherein the heterocyclic group formed by $R_{13}$ and $R_{14}$ is optionally substituted with halogen, —$N_3$, —$NO_2$, —CN, —$OR_{23}$, —$SR_{23}$, —$SO_2R_{23}$, —$SO_2N(R_{23})_2$, —$N(R_{23})_2$, —$COR_{23}$, —$CO_2R_{23}$, —$NR_{23}CO_2R_{23}$, —$NR_{23}COR_{23}$, —$NR_{23}CON(R_{23})_2$, —$CON(R_{23})_2$, or —$(CH_2)_nOR_{23}$;

$R_{15}$ and $R_{16}$ are each independently hydrogen; or linear or branched ($C_1$-$C_6$)-alkyl, ($C_1$-$C_6$)-alkenyl, or ($C_1$-$C_6$)-alkynyl; or both $R_{15}$ and $R_{16}$ may together form a three- to seven-membered heterocyclic group containing up to 3 heteroatoms selected from N, O, or S;

$R_{17}$ is phenyl, 2-pyridyl, 3-pyridyl, or 4-pyridyl;

X is —O—, —$NR_{12}$—, or —$SO_m$—;

each m is independently 0, 1, or 2; and each n is independently 0, 1, 2, 3, or 4.

* * * * *

UNITED STATES PATENT AND TRADEMARK OFFICE
CERTIFICATE OF CORRECTION

| | | |
|---|---|---|
| PATENT NO. | : 7,538,113 B2 | Page 1 of 1 |
| APPLICATION NO. | : 11/354621 | |
| DATED | : May 26, 2009 | |
| INVENTOR(S) | : Pelletier | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 341 days Delete the phrase "by 341 days" and insert -- by 441 days --

Signed and Sealed this

Twenty-third Day of March, 2010

David J. Kappos
*Director of the United States Patent and Trademark Office*